US012590939B2

(12) United States Patent     (10) Patent No.: US 12,590,939 B2

Reisfeld et al.     (45) Date of Patent: Mar. 31, 2026

(54) SYSTEMS, METHODS, AND DEVICES FOR DETECTING HARMFUL ALGAL BLOOMS

(71) Applicant: Colorado State University Research Foundation, Fort Collins, CO (US)

(72) Inventors: Bradley Reisfeld, Wellington, CO (US); Steven J Simske, Fort Collins, CO (US); Edward Hall, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 954 days.

(21) Appl. No.: 17/845,281

(22) Filed: Jun. 21, 2022

(65) Prior Publication Data

US 2022/0404328 A1     Dec. 22, 2022

Related U.S. Application Data

(60) Provisional application No. 63/212,503, filed on Jun. 18, 2021.

(51) Int. Cl.
| | |
|---|---|
| *G01N 33/18* | (2006.01) |
| *B63B 35/00* | (2020.01) |
| *B64U 101/30* | (2023.01) |

(52) U.S. Cl.
CPC ......... *G01N 33/1826* (2013.01); *B63B 35/00* (2013.01); *B63B 2035/007* (2013.01); *B64U 2101/30* (2023.01)

(58) Field of Classification Search
CPC ... B63B 2035/007; B63B 25/00; B63B 35/32; G01N 33/1826; B64U 2101/30; B64U 2101/31
See application file for complete search history.

(56) References Cited

U.S. PATENT DOCUMENTS

| | | | |
|---|---|---|---|
| 9,481,460 | B1 | 11/2016 | Kozloski et al. |
| 10,877,477 | B1 | 12/2020 | Fox et al. |

(Continued)

OTHER PUBLICATIONS

Subramaniam et al., Detecting Trichodesmium blooms in SeaWiFS imagery, Deep-Sea Research II 49, 2002, 107-121. (Year: 2002 ).*

(Continued)

*Primary Examiner* — Kathryn Elizabeth Limbaugh

(74) *Attorney, Agent, or Firm* — Meunier Carlin & Curfman LLC

(57) ABSTRACT

Described herein are systems, methods, and devices for detecting harmful algae blooms. An example system includes autonomous watercraft; and a computing device operably connected to the autonomous watercraft over a network, the computing device including a processor and a memory having computer-executable instructions stored thereon that cause the processor to: surveil a body of water for an algae growth; receive a local condition at the body of water; predict a spread of the algae growth in the body of water based on the local condition; determine a deployment strategy for the autonomous watercraft based on the spread of the algae growth; and transmit one or more control signals to the plurality of autonomous watercraft based on the deployment strategy, where the autonomous watercraft are configured to collect and analyze a plurality of water samples to determine whether the algae growth is a harmful algae bloom.

25 Claims, 30 Drawing Sheets

(56)                    References Cited

U.S. PATENT DOCUMENTS

| | | |
|---|---|---|
| 11,194,348 B2 | 12/2021 | Maor |
| 2017/0231213 A1* | 8/2017 | Gordon ................ G05D 1/0094 43/132.1 |
| 2021/0164954 A1* | 6/2021 | Lewis ................ G01N 33/1886 |

OTHER PUBLICATIONS

"The Jar and Stick Tests," KD HEKS. [Online]. Available: https://www.kdheks.gov/algae-illness/download/Jar_Test.pdf. [Accessed: Mar. 3, 2021.

D. G. Ullman, The Mechanical Design Process, 6th ed. David Ullman LLC.

Wang L, Chen W, Xu D, Shim BS, Zhu Y, Sun F, Liu L, Peng C, Jin Z, Xu C, Kotov NA. Simple, rapid, sensitive, and versatile SWNT-paper sensor for environmental toxin detection competitive with ELISA. Nano Lett. Dec. 2009;9(12):4147-52. doi: 10.1021/nl902368r. PMID: 19928776; PMCID: PMC2793542.

Sarah R. Bickman, Katrina Campbell, Christopher Elliott, Caroline Murphy, Richard O'Kennedy, Philip Papst, and Michael J. Lochhead Environmental Science & Technology 201852 (20), 11691-11698 DOI: 10.1021/acs.est.8b02769.

Grattan LM, Holobaugh S, Morris JG Jr. Harmful Algal Blooms and Public Health. Harmful Algae. Jul. 2016;57(B):2-8. doi: 10.1016/j.hal.2016.05.003. PMID: 27616971; PMCID: PMC5016795.

Adriana Zingone, Henrik Oksfeldt Enevoldsen, The diversity of harmful algal blooms: a challenge for science and management, Ocean & Coastal Management, vol. 43, Issues 8-9, 2000, pp. 725-748, ISSN 0964-5691.

D. M. Anderson, A. D. Cembella, and G. M. Hallegraeff, "Progress in understanding harmful algal blooms (HABs): Paradigm shifts and new technologies for research, monitoring and management," Annual Review of Marine Science, vol. 4, pp. 143-176, Sep. 2011.

Ralston, David K., and Stephanie K. Moore. "Modeling harmful algal blooms in a changing climate." Harmful Algae 91 (2020): 101729.

Chapra SC, Boehlert B, Fant C, Bierman VJ, Henderson J, Mills D, et al. Climate Change Impacts on Harmful Algal Blooms in U.S. Freshwaters: A Screening-Level Assessment. Environ. Sci. Technol. 2017;51:8933-43.

Ng CL, Chen QQ, Chua JJ, Hemond HF.A multi-platform optical sensor for in vivo and invitro algae classification. Sensors (Switzerland). 2017; 17:1-14.

Cunha I, Biltes R, Sales MGF, Vasconcelos V. Aptamer-based biosensors to detect aquatic phycotoxins and cyanotoxins. Sensors (Switzerland).2018;18:1-34.

Wu D, Li R, Zhang F, Liu J.A review on drone-based harmful algae blooms monitoring. Environ. Monit. Assess. 2019;191.

McPartlin DA, Loftus JH, Crawley AS, Silke J, Murphy CS, O'Kennedy RJ. Biosensors for the monitoring of harmful algal blooms. Curr. Opin. Biotechnol. [Internet]. Elsevier Ltd;2017;45:164-9.Available from: http://dx.doi.org/10.1016/j.copbio.2017.02.018.

Beckler JS, Arutunian E, Moore T, Currier B, Milbrandt E, Duncan S. Coastal Harmful Algae Bloom Monitoring via a Sustainable, Sail-Powered Mobile Platform. Front. Mar. Sci.2019;6:1-14.

Shuchman R, Binding C, Leshkevich G, Ortiz J. Remote sensing of harmful algal blooms (HABs) in Lake Erie and other surrounding inland waters: Foreword to special section. J. Great Lakes Res. [Internet]. International Association for Great Lakes Research;2019;45:403-4.Available from: https://doi.org/10.1016/j.jglr.2019.03.015.

Seltenrich N. New tools for detecting, monitoring, and preventing harmful Algal Blooms. Environ. Health Perspect. Public Health Services, US Dept of Health and Human Services; 2014;122.

Birch J. Collecting and processing samples in remote and dangerous places: the Environmental Sample Processor asa case study. PURE Appl. Chem. Genthinerstrasse 13,D-10785 Berlin, Germany:Walter DE Gruyter GMBH;2018;90:1625-30.

Bartram J, Ballance R. Water Quality Monitoring—A Practical Guide to the Design and Implementation of Freshwater Quality Studies and Monitoring Programmes [Internet].United Nations Environment Programme and the World Health Organization; 1996 [cited Sep. 20, 2010].Available from: https://archive.epa.gov/water/archive/web/html/vms50.html.

US Environmental Protection Agency. Sustainability Primer [Internet]. 2015. Available from: https://www.epa.gov/sites/production/files/2015-05/documents/sustainability_primer_v9.pdf.

US Environmental Protection Agency: Office of Water. A Compilation of Costs Data Associated with the Impacts and Control of Nutrient Pollution Internet]. 2015.Available from: https://www.epa.gov/sites/production/files/2015-04/documents/nutrient-economics-report-2015.pdf.

Dodds, W.K., W.W. Bouska, J. L. Eitzmann, T.J. Pilger, K.L. Pitts, A.J. Riley, J.T. Schloesser and DJT. Eutrophication of U.S. Freshwaters: Analysis of Potential Economic Damages. Environ. Sci. Technol. Policy Anal. American Chemical Society; 2009. p. 12-9.

National Centers for Coastal Ocean Science. NCCOS Joins USGS in Congressional Briefing on Harmful Algal Bloom Threats [Internet]. 2017. Available from: https://coastalscience.noaa.gov/news/nccos-joins-usgscongressional-briefing-harmful-algal-bloom-threats/.

* cited by examiner

300

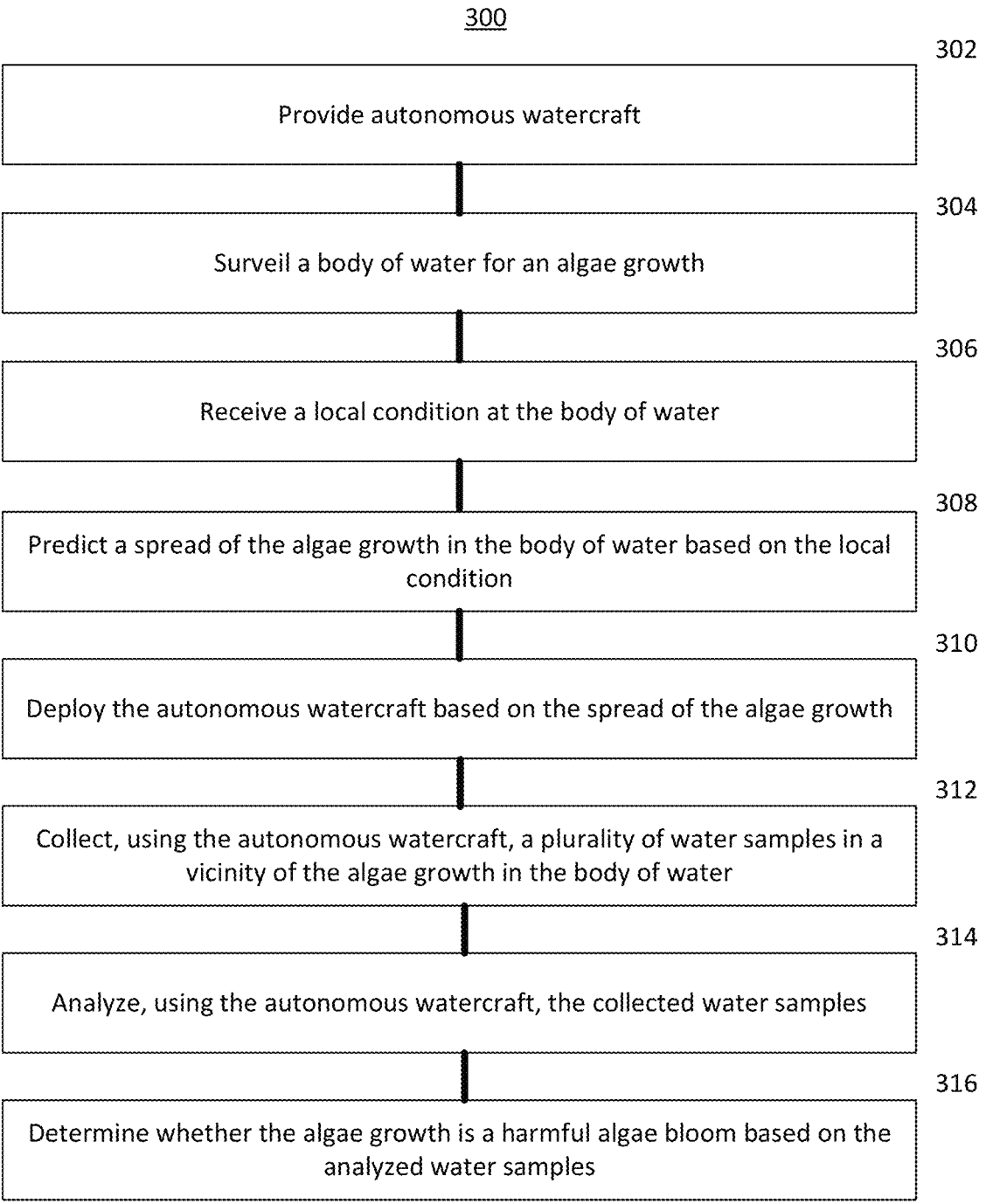

302

Provide autonomous watercraft

304

Surveil a body of water for an algae growth

306

Receive a local condition at the body of water

308

Predict a spread of the algae growth in the body of water based on the local condition

310

Deploy the autonomous watercraft based on the spread of the algae growth

312

Collect, using the autonomous watercraft, a plurality of water samples in a vicinity of the algae growth in the body of water

314

Analyze, using the autonomous watercraft, the collected water samples

316

Determine whether the algae growth is a harmful algae bloom based on the analyzed water samples

*HABs indicators and methods of detection*

| Indicator category | Biomarker or signal for detection | Common methods for detection |
|---|---|---|
| I. Presence of live algae and cyanobacteria | algal biomass and broad community composition, chlorophyll a, phycocyanin, phycoerythrin | fluorescence-based sensors (e.g., in situ pulse amplitude fluorometry), UPLC-UV-MS |
| II. Factor influencing algal and cyanobacterial growth | phosphorus, nitrogen, nitrogen:phosphorus ratios, temperature, turbidity, salinity, pH, dissolved oxygen, light intensity, wind speed | Standard methods in water quality monitoring [11] |
| III. Presence of algal and cyanobacterial toxins | anatoxin-a, azaspiracid, brevetoxin, ciguatoxin, cylindrospermopsin, domoic acid, dinophysistoxin, haemolytic toxin, homoanatoxin, kariotoxin, lyngbyatoxin, maitotoxin, microcystin, nodularin, okadaic acid, pectenotoxin, prymnesin, saxitoxin | LC-MS/MS, HILIC-MS/MS, LC/ESI-MS/MS, ELISA |

Solar Panel

Lid

Rudder Cap

Propellor and Motor

Stepper Motor for Rudder

Rudder

Hull

LiPo Charger

Peristaltic Pump

Lid Latches

GPS Module

Arduino

LiPo Batteries

Test Tube Carousel

1000

1100

1100

1100

1100

SYSTEMS, METHODS, AND DEVICES FOR DETECTING HARMFUL ALGAL BLOOMS

CROSS-REFERENCE TO RELATED APPLICATIONS

This application claims the benefit of U.S. provisional patent application No. 63/212,503, filed on Jun. 18, 2021, and titled "Mobile Autonomous Platform for Harmful Algal Bloom Sensing," the disclosure of which is expressly incorporated herein by reference in its entirety.

STATEMENT REGARDING FEDERALLY FUNDED RESEARCH

This invention was made with government support under grant SU 84015601 awarded by U.S. Environmental Protection Agency. The government has certain rights in the invention.

BACKGROUND

Harmful Algal Blooms (HABs) occur in both freshwater and saltwater, throughout the United States. They are a significant threat to human, animal, and environmental health, through the release of toxins that contaminate bodies of water and water supplies nationwide. As water temperatures rise owing to climate change and "nutrient pollution" continues to escalate, the incidence of HABs is expected to increase [1], as are associated human illnesses, sickness and death of pets, livestock and wildlife, and economic damages related to loss of commercial fishing and recreational revenues, decreased property values, and increased drinking-water treatment costs. For instance, in the summer of 2014, a massive bloom of cyanobacteria (or blue-green algae) in Lake Erie resulted in the closure of drinking water facilities that served 500,000 people in Toledo, OH. Nationwide, cyanotoxins have been implicated in human and animal illness in at least 43 states. In August 2016 alone, at least 19 states had public health advisories owing to cyanotoxins.

Therefore, what is needed are systems, devices, and methods for performing environmental measurements, including systems, devices and methods configured to identify, measure, and predict the location and spread of HABs.

SUMMARY

An example automated system for detecting harmful algae blooms is described herein. The system includes a plurality of autonomous watercraft; and a computing device operably connected to the plurality of autonomous watercraft over a network, the computing device including a processor and a memory, the memory having computer-executable instructions stored thereon that, when executed by the processor, cause the processor to: surveil a body of water for an algae growth; receive a local condition at the body of water; predict a spread of the algae growth in the body of water based on the local condition; determine a deployment strategy for the plurality of autonomous watercraft based on the spread of the algae growth; and transmit one or more control signals to the plurality of autonomous watercraft based on the deployment strategy, where the plurality of autonomous watercraft are configured to collect and analyze a plurality of water samples to determine whether the algae growth is a harmful algae bloom.

Alternatively or additionally, the one or more control signals are configured to deploy the plurality of autonomous watercraft to a location of the algae growth in the body of water.

Alternatively or additionally, the memory has further computer-executable instructions stored thereon that, when executed by the processor, cause the processor to receive, from the plurality of autonomous watercraft, temporally- and spatially-resolved water sample data.

Alternatively or additionally, the memory has further computer-executable instructions stored thereon that, when executed by the processor, cause the processor to overlay the temporally- and spatially-resolved water sample data on a map of the body of water.

Alternatively or additionally, one or more of the plurality of autonomous watercraft include a sensor configured to detect a harmful algae bloom indicator.

Alternatively or additionally, the sensor includes one or more of a fluorescence-based sensor, a phosphorus detection sensor, a nitrogen detection sensor, a temperature sensor, a salinity sensor, a pH sensor, a dissolved oxygen sensor, an ultrasound sensor, a light detection and ranging (LIDAR) sensor, an imaging sensor, or a photoelectric sensor.

Alternatively or additionally, one or more of the plurality of autonomous watercraft includes a sensor system configured to detect a harmful algae bloom indicator. Optionally, the sensor system includes one or more of a liquid chromatography-mass spectrometry (LC-MS) system or an assay system.

Alternatively or additionally, the step of surveilling the body of water for the algae growth includes receiving imaging data from one or more of a satellite, an aircraft, or a drone. Optionally, the step of surveilling the body of water for the algae growth includes receiving imaging data captured by one or more of a Sea-viewing Wide Field-of-view Sensor (SeaWiFS), a moderate resolution imaging spectroradiometer (MODIS), an advanced very-high-resolution radiometer (AVHRR), or an airborne visible/infrared spectrometer (AVIRIS).

Alternatively or additionally, the step of receiving the local condition at the body of water includes receiving weather or water data, the weather or water data comprising one or more of water temperature, water salinity, wind speed and/or direction, or water current speed and/or direction.

Alternatively or additionally, the step of predicting the spread of the algae growth in the body of water includes using an ensemble model.

Alternatively or additionally, the step of determining the deployment strategy for the plurality of autonomous watercraft includes using a resource mapping model. Optionally, the resource mapping model is a Markov chain model, a Monte Carlo simulation model, a random forest model, a deep learning model, agent-based model, or an evolutionary model.

Alternatively or additionally, the system includes one or more autonomous aerial vehicles (UAVs) operably coupled to the computing device over the network, where the one or more UAVs are configured to surveil the body of water for the algae growth and/or collect and analyze the water samples.

An example method for detecting harmful algae blooms is described herein. The method includes providing a plurality of autonomous watercraft; surveilling a body of water for an algae growth; receiving a local condition at the body of water; predicting a spread of the algae growth in the body of water based on the local condition; deploying the plurality of autonomous watercraft based on the spread of the algae growth; collecting, using the plurality of autonomous water-craft, a plurality of water samples in a vicinity of the algae growth in the body of water; analyzing, using the plurality of autonomous watercraft, the collected water samples; and determining whether the algae growth is a harmful algae bloom based on the analyzed water samples.

Alternatively or additionally, the method includes receiving, from the plurality of autonomous watercraft, tempo-rally- and spatially-resolved water sample data. Optionally, the method further includes overlaying the temporally- and spatially-resolved water sample data on a map of the body of water.

Alternatively or additionally, the step of surveilling the body of water for the algae growth includes receiving imaging data from one or more of a satellite, an aircraft, or a drone. Optionally, the step of surveilling the body of water for the algae growth includes receiving imaging data cap-tured by one or more of a Sea-viewing Wide Field-of-view Sensor (SeaWiFS), a moderate resolution imaging spectro-radiometer (MODIS), an advanced very-high-resolution radiometer (AVHRR), or an airborne visible/infrared spec-trometer (AVIRIS).

Alternatively or additionally, the step of receiving the local condition at the body of water includes receiving weather or water data, the weather or water data comprising one or more of water temperature, water salinity, wind speed and/or direction, or water current speed and/or direction.

Alternatively or additionally, the step of predicting the spread of the algae growth in the body of water includes using an ensemble model.

Alternatively or additionally, the step of determining the deployment strategy for the plurality of autonomous water-craft includes using a resource mapping model. Optionally, the resource mapping model is a Markov chain model, a Monte Carlo simulation model, a random forest model, a deep learning model, agent-based model, or evolutionary model.

A computing system for detecting harmful algae blooms is described herein. The system includes: a processor; and a memory operably coupled to the processor, the memory having computer-executable instructions stored thereon that, when executed by the processor, cause the processor to: surveil a body of water for an algae growth; receive a local condition at the body of water; predict a spread of the algae growth in the body of water based on the local condition; determine a deployment strategy for a plurality of autono-mous watercraft based on the spread of the algae growth; and transmit one or more control signals to the plurality of autonomous watercraft based on the deployment strategy, where the plurality of autonomous watercraft are configured to collect and analyze a plurality of water samples to determine whether the algae growth is a harmful algae bloom.

An unmanned autonomous watercraft is described herein. The unmanned autonomous watercraft includes a computing system comprising a memory and a processor; a networking module comprising an antenna and operably connected to the computing system; a navigation module operably con-nected to the computing system, where the navigation mod-ule includes a navigation antenna; a power source; a pro-pulsion device; and a sample collection device.

Alternatively or additionally, the sample collection device is a multi-cartridge stack or conveyor system.

Alternatively or additionally, the sample collection device is a sample collection carousel. Alternatively or additionally, the sample collection carousel includes a base with a top surface and a bottom surface and a divot formed in the top surface; a test tube rack positioned on the base; one or more test tubes retained in the test tube rack, where turning the test tube rack relative to the base causes at least one of the test tubes retained in the test tube rack to be positioned in the divot formed in the top surface of the base. Optionally, the sample collection carousel further includes a tube with an inlet and an outlet, where the outlet is positioned to fill a test tube retained in the test tube rack and positioned in the divot.

Alternatively or additionally, the watercraft includes a peristaltic pump configured to move a sample to the outlet of the tube. Optionally, when the autonomous watercraft is positioned in a body of water, the system is configured to pump water from the body of water through the tube and into the test tube positioned in the divot.

Alternatively or additionally, the sample collection car-ousel includes a sensor configured to measure a property of the samples in a test tube retained in the test tube rack. Optionally, the sensor includes a fluorescence or turbidity probe. Optionally, the sensor is configured to detect a harmful algae bloom indicator. Alternatively or additionally, the sensor includes one or more of a fluorescence-based sensor, a phosphorus detection sensor, a nitrogen detection sensor, a temperature sensor, a salinity sensor, a pH sensor, a dissolved oxygen sensor, an ultrasound sensor, a light detection and ranging (LIDAR) sensor, an imaging sensor, or a photoelectric sensor. Alternatively or additionally, the sensor includes one or more of a liquid chromatography-mass spectrometry (LC-MS) system or an assay system. Optionally, the sensor includes a paper-based microfluidic device.

Alternatively or additionally, the power source includes a solar panel, lithium ion battery, and a lithium ion battery charger configured to charge the lithium ion battery by the solar panel.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed descrip-tion. It is intended that all such additional systems, methods, features and/or advantages be included within this descrip-tion and be protected by the accompanying claims.

BRIEF DESCRIPTION OF THE DRAWINGS

The components in the drawings are not necessarily to scale relative to each other. Like reference numerals desig-nate corresponding parts throughout the several views.

FIG. 3 illustrates a method of detecting harmful algae blooms, according to an implementation of the present disclosure.

FIG. 4B illustrates a table of biomarkers and methods that can be used to detect harmful algae, according to imple-mentations of the present disclosure.

FIG. 6A is a perspective view of the watercraft. FIG. 6B is an exploded perspective view illustrating components of the watercraft. FIG. 6C is an exploded side view illustrating components of the watercraft.

FIG. 8A illustrates a perspective view of a hull design. FIG. 8B illustrates a perspective view of a hull design formed with 3D printed shapes. FIG. 8C illustrates a perspective view of the completed watercraft.

FIG. 11A is a perspective view of a hull that has been sanded. FIG. 11B is a perspective view of a hull that has been painted. FIG. 11C is a side view of a hull that has been painted. FIG. 11D is a top view of the inside of the watercraft illustrated in FIG. 11C. FIG. 11E is a perspective view of the watercraft illustrated in FIG. 11C. FIG. 11F is a top view of the watercraft illustrated in FIG. 11C. FIG. 11G is a perspective view of the bottom of the watercraft illustrated in FIG. 11C. FIG. 11H is a view from below of the bottom of the watercraft illustrated in FIG. 11C. FIG. 11I is another perspective view of the watercraft illustrated in FIG. 11C.

FIG. 12 illustrates an example computing device.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for performing certain measurements (e.g. concentrations of algae), it will become evident to those skilled in the art that the implementations are not limited thereto, but are applicable to performing any kind of environmental measurement.

Figure 1:
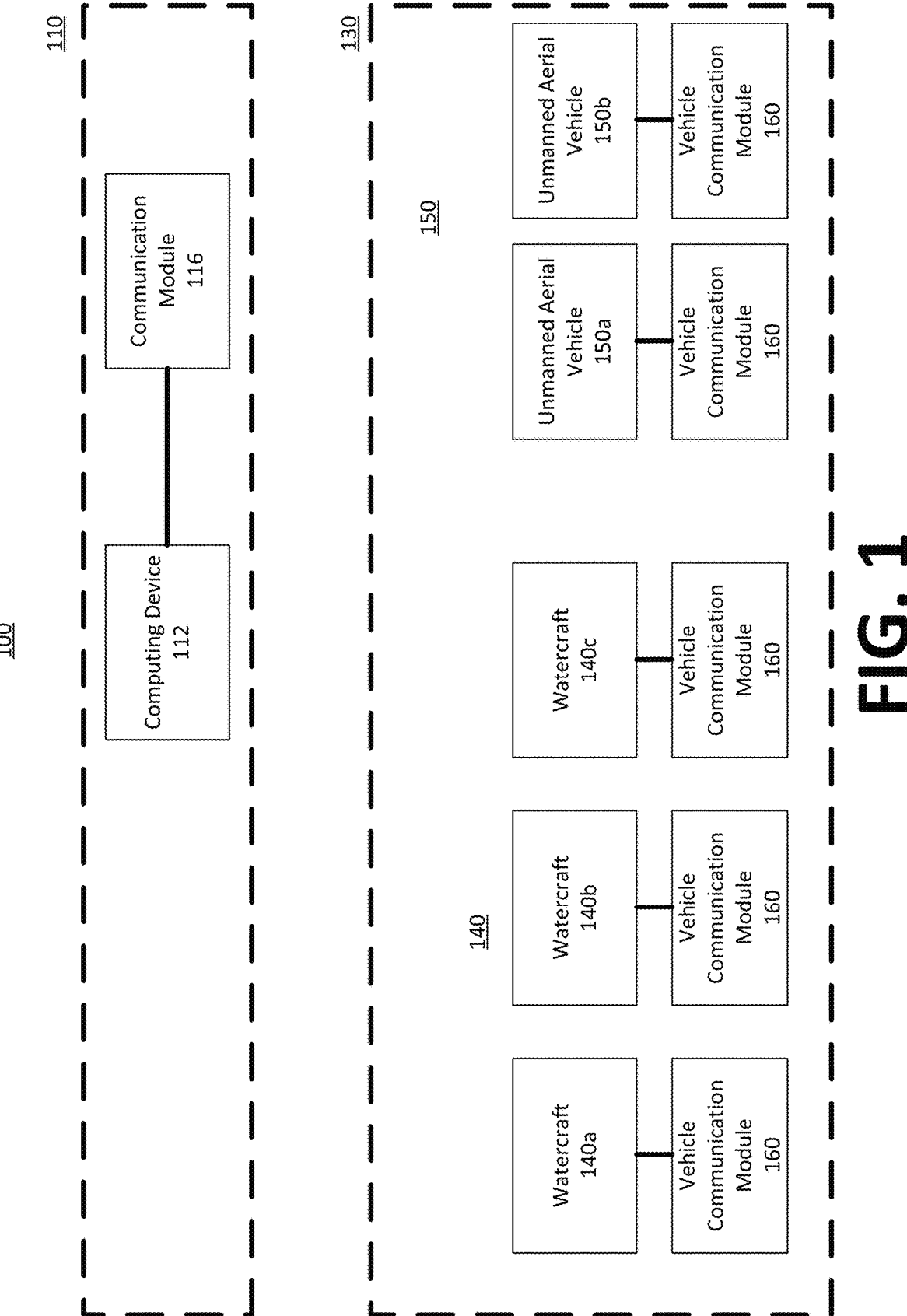
FIG. 1 illustrates a block diagram of a system for detect-ing harmful algae blooms, according to an implementation of the present disclosure.

FIG. 1 illustrates an example system 100 for detecting harmful algae blooms. The system 100 can include a control system 110 configured to send and receive information from one or more unmanned vehicles 130. The system 100 and unmanned vehicles 130 can be connected by one or more communication links. This disclosure contemplates the communication links are any suitable communication link. For example, a communication link may be implemented by any medium that facilitates data exchange including, but not limited to, wired, wireless and optical links. Example communication links include, but are not limited to, a local area network (LAN), a wireless local area network (WLAN), a wide area network (WAN), a metropolitan area network (MAN), Ethernet, the Internet, or any other wired or wireless link such as WiFi, WiMax, 3G, 4G, or 5G. The control system 110 can include a computing device 112, which can include some or all of the components described with reference to FIG. 12. Additionally, the control system 110 can include a communications module 116 configured to perform wireless communication with one or more other communications modules. Non-limiting examples of wireless communications protocols that can be used include Bluetooth, long term evolution (LTE), MESH, WiFi, LoRa, and other wireless communication protocols.

The system 100 can also include one or more unmanned vehicles 130. The unmanned vehicles 130 can include watercraft 140a, 140b, 140c (referred to herein collectively and individually as watercraft 140) (described in greater detail with reference to FIG. 2) and unmanned aerial vehicles (UAVs) 150a, 150b, 150c (referred to herein collectively and individually as unmanned aerial vehicle or vehicles 150) (described herein with reference to FIG. 5B). The control system 110 can transmit information to the unmanned vehicles 130, and the unmanned vehicles 130 can transmit information to the control system 110. As shown in FIG. 1, each of the unmanned vehicles 130 can include a vehicle communications module 160. It should be understood that the number of watercraft 140 and unmanned aerial vehicles 150 shown in FIG. 1 are provided only as an example. The present disclosure contemplates that any number of watercraft 140 and/or unmanned aerial vehicles 150 can be used. Additionally, each of the unmanned vehicles 130 can include a computing device (not shown), e.g., the computing device illustrated in FIG. 12. The computing device can be configured to control the unmanned vehicle, for example in response to the signals received by the vehicle communication module 160. It should be understood that, in some implementations, the vehicle communication module 160 can be a receiver, a transmitter, or a transceiver. Additionally, the present disclosure contemplates that the unmanned vehicles can include multiple communication modules (e.g., a first communication module can be a transmitter and a second communication module can be a receiver).

The computing device 112 can be configured to implement the method described with respect to FIG. 3 for predicting the location of algae blooms and controlling the unmanned vehicles 130 based on the predicted location of the algae bloom.

Figure 2:
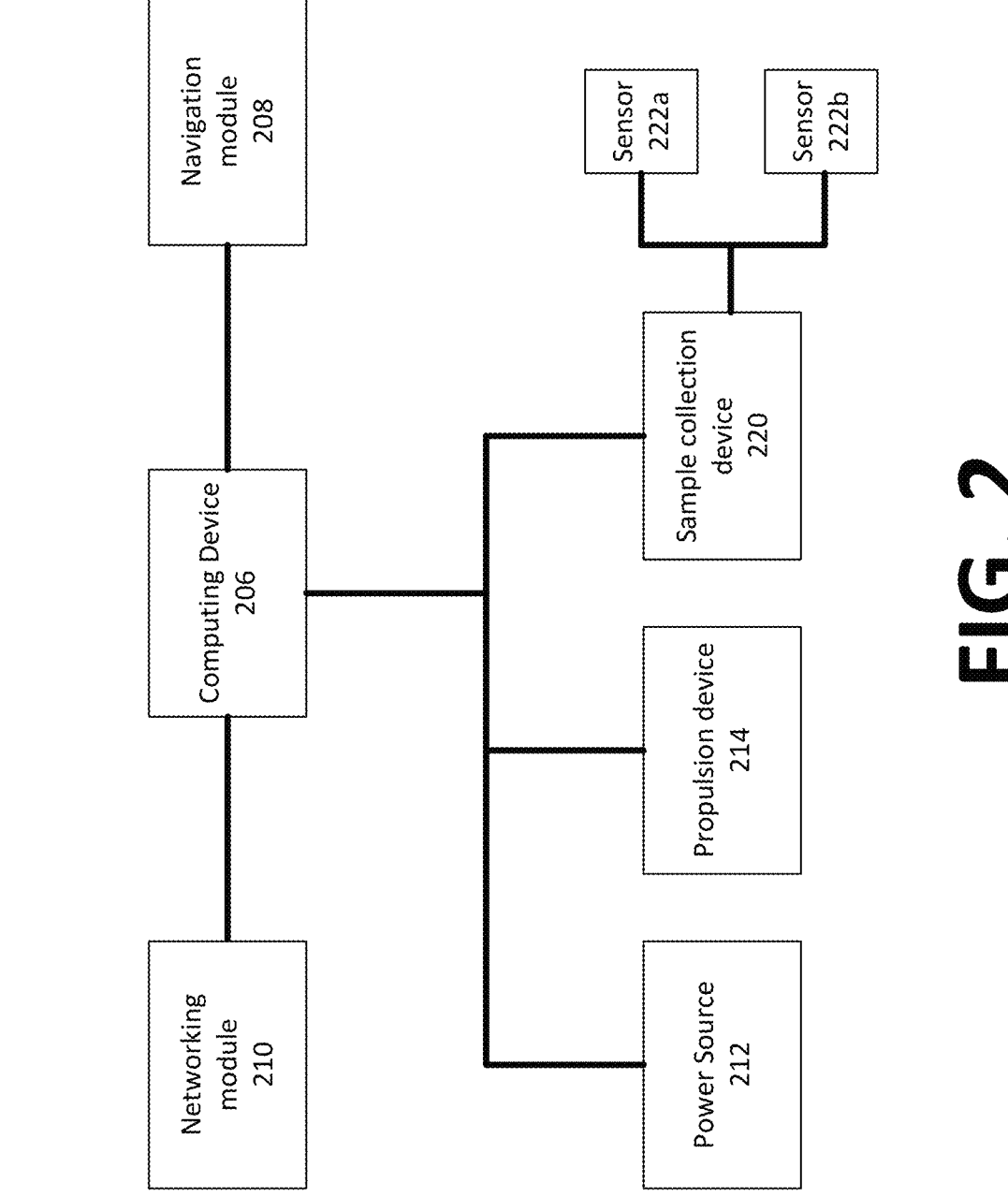
FIG. 2 illustrates a system block diagram of an imple-mentation of a watercraft that can be used as part of the system illustrated in FIG. 1.

FIG. 2 illustrates an example system block diagram for a watercraft 240, according to an implementation of the present disclosure. The watercraft 240 can optionally be used as the watercraft for implementing the system 100 illustrated in FIG. 1. The watercraft 240 can include a computing device 206 that can control the watercraft 240. As described with reference to FIG. 1, the computing device 206 can include any or all of the components illustrated in FIG. 12. The computing device 206 can be configured to receive information from a navigation module 208. The navigation module 208 can track the location of the watercraft 140, for example by using the global positioning system (GPS). The navigation module 208 can include one or more GPS antennas. It should be understood that GPS is provided only as an example navigation technique. This disclosure contemplates that the navigation module 208 can be configured to use other known navigation techniques. Additionally, the watercraft 240 can include a networking module 210. The networking module can include one or more antennas, and can be configured to send and/or receive transmissions. Non-limiting examples of communications protocols that can be used by the wireless communications module include Bluetooth, long term evolution (LTE), MESH, WiFi, LoRa, and other wireless communication protocols.

The watercraft 240 can also include a power source 212. In some implementations, the power source 212 includes both an electric battery and a solar panel, where the solar panel is configured to recharge the battery over time. The power source can be operably coupled to provide power to any of the components of the watercraft (e.g., any of the other components illustrated in FIG. 2). The watercraft 240 can also include charging/power management circuits configured to boost and/or reduce the voltages and currents in the device to provide the appropriate voltages/currents to each component shown in FIG. 2. E.g., if the output voltage of the solar panel is lower than the battery voltage, then a battery charge circuit can be used to step up the voltage to charge the battery. The power source 212 can also include energy scavenging systems including wind energy systems and solar energy systems. Additional non-limiting examples of energy scavenging systems include Peltier devices that can be used to generate power using a difference in temperature between water and air, and vibration energy scavengers that can collect energy from waves around the watercraft. It should also be understood that the computing device 206 can be configured to steer or navigate the watercraft to increase the power generated by any energy scavenging devices or other power sources 212. For example, the computing device can be configured to recharge the watercraft 240 by turning toward the sun, into the wind, into choppy water to increase the effectiveness of one or more of the power sources 212. Additionally, in systems (e.g., the system 100 illustrated in FIG. 1) using autonomous watercraft, it should be understood that the system can be configured so that not all of the watercraft are recharging at the same time (e.g., a minimum number of watercraft can be monitoring, while the remaining watercraft recharge).

Additionally, the watercraft 240 can include a propulsion device 214. The propulsion device can include one or more thrusters (e.g., electric thrusters). It should be understood that thrusters are provided only as an example propulsion device. This disclosure contemplates using other mechanisms for propulsion, e.g., propellers. The propulsion device can also optionally include steering devices, for example rudders or fins.

The watercraft 240 can also include a sample collection device 220. In some implementations, the sample collection device is a carousel including one or more test tubes (illustrated in FIGS. 7A-7F). Alternatively or additionally, the sample collection device 220 can include cartridges and be configured to collect samples into cartridges that can be stacked and stored in the watercraft 140. As another example, in some implementations, the sample collection device 220 can include a conveyor system to move test tubes and/or cartridges through the watercraft 240. The sample collection device 220 can also include tubing configured to draw water from around the watercraft and a pump (e.g., a peristaltic pump) configured to draw water into the sample collection device 220, and to fill cartridges and/or test tubes in the sample collection device. Additionally, the present disclosure contemplates the sample collection device 220 can be configured to move water from the sample collection device to the sensors 222a, 222b (referred to herein collectively and individually as sensor or sensors 222). It should be understood that the number of sensors 222 shown in FIG. 2 are provided only as an example. The present disclosure contemplates that any number of sensors 222 can be used. Alternatively, or additionally, the sensors 222 can be integrated into the sample collection device 220 to sense the contents of the cartridges or test tubes.

The sample collection device 220 can include one or more sensors 222 configured to measure the properties of the samples. The sensors 222 can be configured to detect indicators of harmful algae blooms. For example, the sensors can include a liquid chromatography-mass spectrometry (LC-MS) sensor system or an assay sensor system. Non-limiting example LC-MS sensor systems include liquid chromatography with tandem mass spectrometry (LC-MS/MS), ultra performance liquid chromatography with ultraviolet mass spectrometry (UPLC-UV/MS), hydrophilic interaction chromatography with tandem mass spectrometry (HILIC-MS/MS), and liquid chromatography electrospray ionization with tandem mass spectrometry (LC/ESI-MS/MS) systems. Non-limiting example assay sensor systems include enzyme-linked immunosorbent assay (ELISA) systems. Other sensors that can be used include a fluorescence-based sensor, a phosphorus detection sensor, a nitrogen detection sensor, a temperature sensor, a salinity sensor, a pH sensor, a dissolved oxygen sensor, ultrasound sensor, LIDAR sensor, imaging sensor, or a photoelectric sensor. Other sensor 222 examples include, fluorescence or turbidity probes. The sensor 222 can also be a paper based or electronic microfluidic device. The present disclosure contemplates that combinations of any or all of the sensors 222 described herein can be used in various implementations of the present disclosure. Additionally, the present disclosure contemplates that the measurements from the sensors 222 can be transmitted to the computing device, and/or through the networking module.

The watercraft 240 or unmanned aerial vehicles 150 of the present disclosure can be configured to implement a path-finding algorithm with the ability to maneuver the unmanned vehicles 130 around bodies of water. In some implementations, the pathfinding algorithm can be based on research from ArduPilot or other pathfinding algorithms for unmanned vehicles. Additionally, the unmanned watercraft 140 and UAVs 150 described herein can transmit data to an offsite computing device (e.g., a smartphone, tablet, laptop, or other mobile computing device). In some implementations, the offsite computing device (not shown) is the computing device 112 of the control system 110 illustrated in FIG. 1. The data transmitted can include information about the position and orientation of the unmanned vehicle, the locations where the sensors collected data, the data the sensors collected, and alert messages based on the status of the drone. Additionally, the data can include status information, e.g., information indicating that the unmanned vehicle is ready to be retrieved by an operator.

FIG. 3 illustrates a method 300 for detecting harmful algae blooms, according to an implementation of the present disclosure. The method 300 can include providing 302 autonomous watercraft, for example the autonomous watercraft described with reference to FIGS. 1 and 2. In some implementations, autonomous aerial vehicles can be provided in addition to the watercraft, for example as described with reference to FIG. 1.

The method 300 can also include surveilling 304 the body of water for algae growth. Surveilling the body of water can include using remote sensing techniques to estimate various parameters of the body of water. Surveilling 304 the body of water can be performed by satellites, or by aerial vehicles (e.g., manned airplanes or unmanned aerial vehicles/drones), or by stationary sensors. Surveilling 304 the body of water can include using one or more types of surveillance and aggregating the information. Additionally, surveilling 304 the body of water can be performed by accessing a database including information about the body of water.

The method 300 can also include receiving 306 a local condition at the body of water. As a non-limiting example, the local condition can include information about the temperature of the body of water, current speed/direction in the body of water, wind conditions (speed and/or direction), and/or the color of the body of water. Additional examples of local condition information include other weather data, and water salinity information. The received 306 information can be temporally and/or spatially resolved. In some implementations, the temporally and/or spatially resolved information can be displayed to a user, for example as an overlay on a map. The method can include using the spatially and/or temporally resolved data for a variety of applications. Non-limiting example applications include monitoring the conditions of swimming pools, fish nurseries, water treatment pools, nuclear plant cooling pools, canals, irrigation channels, and harbor fronts. It should be understood that these alternative implementations can be used in applications for detecting HABs, as well as alternative applications like monitoring water quality or detecting invasive species.

The method 300 can also include predicting 308 a spread of the algae growth in the body of water based on the local condition. For example, predicting 308 can include estimating a spread of the algae growth using information about the wind and current in the body of water. Alternatively or additionally, the spread of the algae growth in the body of water can be predicted based on hydrodynamics, water conditions, atmospheric conditions, algae growth. Optionally, the spread of the algae growth in the body of water can be predicting using an ensemble model, see e.g., Ralston, David K., and Stephanie K. Moore. "Modeling harmful algal blooms in a changing climate." *Harmful Algae* 91 (2020): 101729. It should be understood that the above techniques are provided only as examples and that this disclosure contemplates using any known technique to predict the spread of the algae growth in the body of water.

The method 300 can also include deploying 310 the autonomous watercraft to collect 312 water samples in or near the vicinity of the algae growth that is estimated using the local condition of the body of water. In some implementations, the autonomous watercraft are deployed to a current location of the algae growth. Alternatively or additionally, in some implementations, the autonomous watercraft are deployed to a future predicted location of the algae growth. It should be understood that autonomous watercraft can be deployed to different locations in the body of water. Deploying 310 the autonomous watercraft can include applying a resource mapping model to determine where each of the autonomous watercraft should be sent. Non-limiting examples of resource mapping models that can be used in implementations of the present disclosure include Markov chain models, Monte Carlo simulation models, random forest models, and/or deep learning models, agent-based models, or evolutionary models.

The sampled can be analyzed 314, for example by using one or more sensors of the autonomous watercraft. The sensors can be sensors configured to measure properties of the algae, e.g., the sensors described with reference to FIG. 2. Whether the algae growth is a harmful algae bloom can be determined 316 based on the water samples. Harmful algal blooms cause negative impacts to other organisms in the surrounding environment, for example by producing toxins and/or other means to damage organisms. Biomarkers (e.g., see Table shown in FIG. 4B) of HABs can be detected using one or more sensors of the autonomous watercraft. Thus, the method of FIG. 3 is capable of distinguishing HABs from ordinary algal blooms.

The information from the sample that is analyzed 314 and the determination 316 of whether the algae growth is a harmful algae bloom can be temporally and/or spatially resolved. For example, the information about the sample can include where the sample was taken (spatial information) and when that information was taken (temporal information). In some implementations, the method can include receiving the temporal and/or spatial information from the watercraft. Additionally, the temporal and/or spatial information can be overlaid onto a map of the body of water.

EXAMPLE 1

An example system for sensing harmful algal blooms is described herein.

There are a spectrum of approaches and technologies for sensing and monitoring HABs and more benign Abs (algal blooms) [2-9].

Imaging: Satellites, manned aircraft, and drones can be used to acquire images that are used for HABs research and monitoring. These images can be combined with weather data and machine learning algorithms for forecasting the likelihood of algal blooms. Imaging instruments and modalities include Sea-viewing Wide Field-of-view Sensor (Sea-WiFS), Moderate Resolution Imaging Spectroradiometer (MODIS), Advanced Very-High-Resolution Radiometer (AVHRR), and Airborne hyperspectral. Imaging methodologies are easily able to cover large geographical areas and can give a time-based component to analyses. However, these methods are not able to discriminate HABs from ABs, have limited resolution that makes them only applicable to larger bodies of water, require expertise and special resources, and are not generally practical for small, local water resources. In addition, aircraft and drones make use of fuel from non-sustainable sources and have a significant carbon footprint. Maintenance, reliability, and cost are also of concern for satellite and aircraft-based modalities of image acquisition.

On-site sampling: Using onshore personnel or manned watercraft, water and algae samples can be taken at specific accessible locations within a body of water. These samples are normally brought back to a laboratory for analytical testing and analysis. Analytical methods on these samples can include in situ pulse amplitude fluorometry, LC-MS/MS, ultra-performance liquid chromatography coupled with ultraviolet detection and mass spectrometry, ELISA, ELISA-ADDA, and qPCR. Depending on the analytical equipment available, on-site sampling can provide good discrimination of HABs versus ABs. However, such methods are very labor intensive, will only obtain single point measurements in time and space, and expertise is required in sampling procedures and analyses to assure reproducibility and uniformity across labs. In addition, watercraft make use of fuel from non-sustainable sources and have a significant carbon footprint. In situ samplers and analyzers: In situ samplers are generally deployed via ships and are anchored securely into a strategic position within a body of water. These probes are often autonomous and can perform auto-sampling and sophisticated automated analyses. For example, versions of the NOAA Environmental Sample Processor (or "lab in a can") [10] contains various analytical modules (e.g., surface plasmon resonance, digital droplet PCR, and total internal reflection fluorescence), to identify groups of bacteria, harmful algal species, algal biotoxins, and other biomarkers associated with HABs. With proper maintenance and calibration, these devices can take reproducible readings at frequent intervals. However, they are very expensive to procure, deploy, and operate and because of this, are generally not feasible for widespread adoption.

The example implementation of the present disclosure described herein can facilitate widespread adoption of the MAP-HAB S concept. In particular, implementations of the present disclosure referred to as the "Mobile Autonomous Platform for Harmful Algal Bloom Sensing" (also referred to herein as "MAP-HABS" or "HABsBot") can utilize as many commodity parts as possible to minimize costs, be capable of moving and sampling across a body of water in a prescribed or autonomous manner, discriminate between HABs and ABs, sample and analyze in real time to give temporally- and spatially-resolved data, be deployable by a 1- or 2-person crew, may utilize a main power source that is sustainable, and be modular and adaptable over time.

Device Elements and Design

Figure 4A:
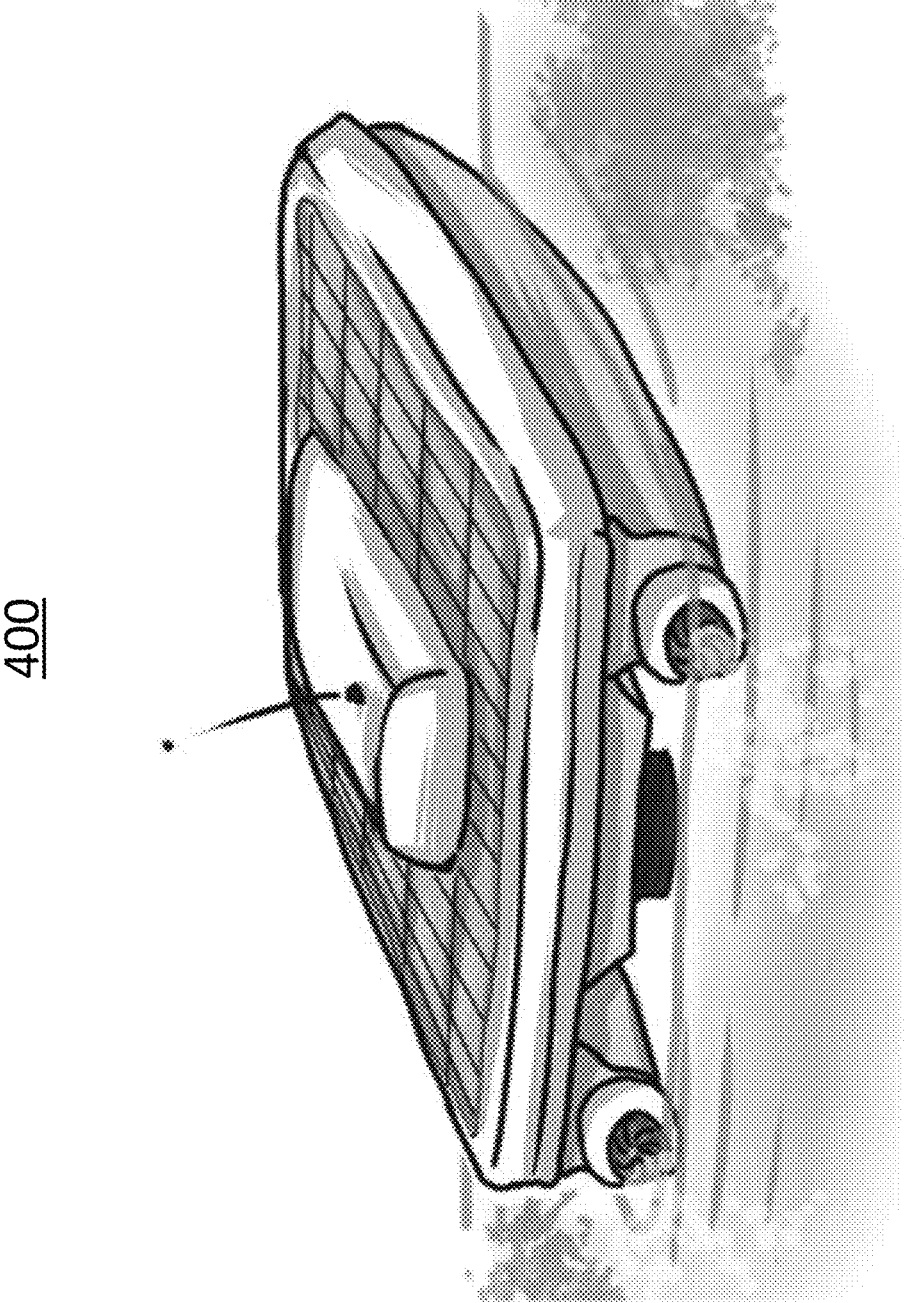
FIG. 4A illustrates a perspective view of a watercraft that can be used to detect harmful algae blooms, according to implementations of the present disclosure.

An example implementation of the present disclosure referred to as MAP-HABS or HABsBot is described herein. The example implementation can include several major components, including but not limited to a case, chassis, sampler, sensor module, power generation system, electronics and communications system, and propulsion and steering system. FIG. 4A illustrates a perspective view of the watercraft 400.

Sensor module: As shown in FIG. 2B, there are multiple specific and non-specific indicators of the presence of HABs. For detection and prediction of HABs, the sensor system can incorporate methods for detecting indicators in such categories.

Power generation system: In the example implementation, power can be generated using photovoltaic panels with a rechargeable battery backup. Inexpensive polycrystalline panels are commercially available in a variety of sizes and weights, with efficiencies ranging from about 15-23%. Implementations of the present disclosure can include any type of battery technology (e.g., Lithium-ion or nickel-cadmium, or lead-acid), and it should be understood that different battery technologies can include different properties including sustainability, power, weight, and size that can be suitable for different implementations.

Electronics and communications system: The example implementation can include electronics that can interconnect the power generation, sensors, sampler, propulsion, data acquisition, and communication elements. Data can be stored in an onboard logger and transmitted wirelessly to a monitoring station. Wireless communication can utilize Wireless RF Technology (e.g., the wireless RF protocol sold under the trademark LoRa). In some implementations, the wireless RF technology can be a wireless technology capable of long range, low power consumption, and secure data transmission. Additionally, in some implementations, the electronics can be configured to use data formats compatible with national systems (e.g., the National Centers for Coastal Ocean Science (NCCOS) 'Harmful Algal Bloom Monitoring System' and the Center for Disease Control and Prevention (CDC) 'One Health Harmful Algal Bloom System').

Propulsion and steering system: The present disclosure contemplates that a variety of propulsion and steering systems can be used with the watercraft 400 illustrated in FIG. 4. Non-limiting examples of propulsion include water-cooled brushless DC marine motors coupled to propellers or water jet drives. Steering can be via rudders or nozzles with electronic actuators.

EXAMPLE 2

Non-limiting example implementations of drones entitled "HABs Bot" were constructed. The example implementations include designs for unmanned aerial vehicles (UAV's) and unmanned watercraft, as described below.

An example implementation of the HABs Bot is an autonomous surface drone equipped with sensors designed to detect and distinguish between harmful and non-harmful algal species. The example implementation can contain a two-staged detection system and provide an automated means of monitoring a water body of interest. Stage one of the detection system can employ a Specialized Continuous Monitoring System (SCMS) aimed at monitoring the cell densities present in a given water body.

The onboard logic can use datasets provided by the SCMS to determine when a particular area of water has a high probability of containing toxic algae species. Should an area of water be flagged as having a high probability of contamination, stage two of the detection system can be used to test the water for the presence of microcystin and cylindrospermopsin. This will be done with a pump and tube carousel that will collect samples of water from freshwater sources.

Carbon nanotubes coated with antibodies for these toxins will be dipped into water samples and an electrochemical test will be administered via a potentiostat to determine toxin concentrations of the water. This method of toxin screening is known as a micro PAD test. The contained tubes of water also allow the water to be brought back to a lab to do more accurate tests.

A single 50 W photovoltaic cell can provide 100% of the power demands for the system. The solar panel can charge LiPo batteries when energy production exceeds demand and can provide power to the drone when demand exceeds production. Propulsion can be provided by a single thruster (e.g., a thruster sold under the trademark T200 by Blue Robotics). All control systems and logic can be provided by a single Raspberry Pi. A LoRa GPS hat can be used to receive and transmit autonomous navigation feedback, SCMS data, and micro PAD test results. Machine learning algorithms can be used in conjunction with satellite imagery to provide the drone with a predetermined surveillance path and to test the chemical sensors.

An example technique for HAB detection include the use of "the jar and stick test" [1A] where algae are visually inspected to determine the probability the algae hazard level. This device aims to provide communities with a scientific and accurate means of monitoring the public health risk of HABs in freshwater sources. This device can be deployable in a variety of settings including communal ponds, agricultural water sources, lakes, and other areas where HABs are likely to occur. The HABs Bot can provide users with definitive evidence of the presence of microcystin and cylindrospermopsin in a body of water. The data provided by this drone can help scientists better predict harmful algae blooms and prevent outbreaks before they occur.

Design 1.0

Figure 5A:
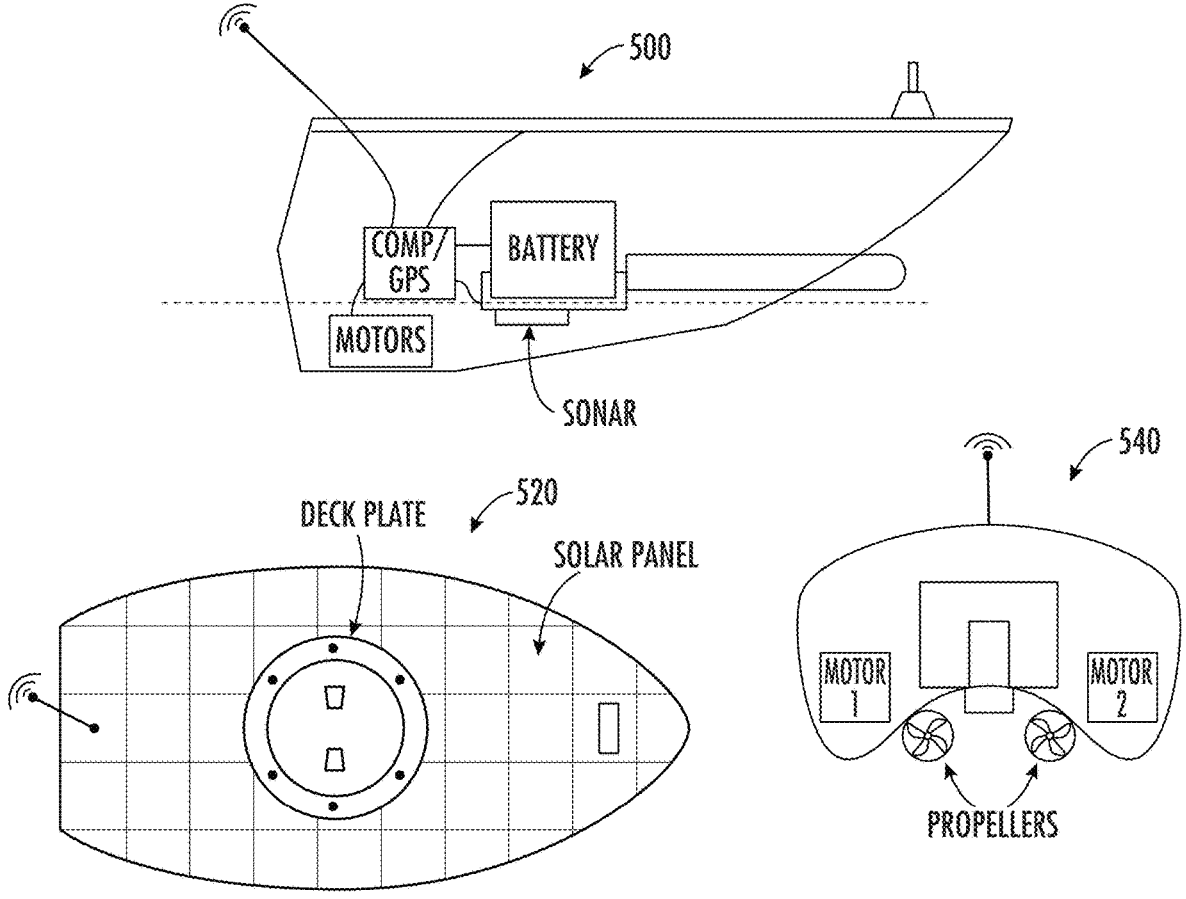
FIG. 5A illustrates perspective views of a watercraft that can be used to detect harmful algae blooms, according to implementations of the present disclosure.

An example implementation of an unmanned watercraft was titled "Design 1.0." The example implementation is an autonomous boat drone. The example surface drone is 3-5 ft wide and 2-3 ft long. The system can be powered by a 40 W solar array, and lithium battery. Two thrusters (e.g., thrusters sold by Blue Robotics under the trademark T200) can move the drone. In the example implementation, an in Situ Aqua Troll continuous sensor was used. This sensor can detect if an Algal Bloom is present but can require additional information to determine a HAB from a non-HAB through the presence of toxins. For the autonomous navigation, machine learning can be used to create a border around a lake (though color mapping), then a pathfinding algorithm could be used to move the boat around within the border of the lake. This method can also rely on having a sonar and lidar sensor that could detect any upcoming obstacles, like rocks, that the drone would need to avoid at the last minute. Finally, LoRa can send the data back to the user. FIG. 5A illustrates a side view 500, a top view 520, and a rear view 540 of an example implementation of the Design 1.0.

Figure 5B:
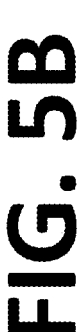
FIG. 5B illustrates an aerial vehicle that can be used to detect harmful algae blooms, according to implementations of the present disclosure.

With reference to FIG. 5B, an example implementation of an unmanned aerial vehicle 550 (i.e., aerial drone or UAV) is also described herein. Using an aerial approach to HAB detection, a drone can use satellite imagery and machine learning algorithms can generate probability maps of a given body of water. This algorithm can analyze satellite images of lakes and ponds by determining the probability the images' pigments correlated to the known pigments of HABs. The algorithm can then geotag an area of water that was deemed to have a high probability of containing a HAB. The second line of detection can utilize an UAV to perform a toxin screening of the water. These steps can be performed at regular intervals (e.g., weekly).

This example implementation of an unmanned aerial vehicle can maximize the range of surveillance for HABs while minimizing the labor required. Sample testing can be performed using a pneumatic pump and four-way electric solenoid valve system onboard the UAV. The drone was designed to hover above the surface of a water body, deploy a sampling hose, engage its pump to collect a sample into a single vessel, then return to a centralized base to perform a micro PAD test. Equipped with four independent sample vessels and up to 1 kg of weight allotted for a payload, the UAV was designed with the intent to collect multiple samples per flight.

The example implementation of a surface drone can be operable in a wider range of weather conditions as compared to the aerial design.

The present disclosure contemplates that the sensing methods described with reference to the UAV and unmanned watercraft can be used interchangeably (i.e., sensors from the UAV can be used on the unmanned watercraft, and vice-versa). For example, a unmanned watercraft (e.g., the unmanned watercraft illustrated in FIG. 5A) can include the SCMS as a primary screening method and micro PAD testing to determine the toxin content of the water.

In some implementations, the drone can contain a solar panel on its roof which can provide 100% of the drone's power requirements. This solar panel was increased in generation capabilities from 40 W to 100 W in order to ensure the drone has enough power for long surveillance periods.

In some implementations, the power consumption of the surface design can be reduced by only including one thruster. In implementations with more than one thruster, steering of the drone can be provided by changing the power output of each thruster. In some implementations, including implementations with only one thruster, steering can be performed by rotating the one or more thrusters, or by a rudder. The thrusters and/or rudder can be configured to be turned by a motor (e.g., a stepper motor).

Both the aerial and surface designs illustrated in FIGS. 5A and 5B can include lidar and sonar modules. In some implementations, the lidar and/or sonar modules can be used for obstacle avoidance. Additionally, implementations can be controlled based on satellite imagery, including by providing a predetermined path.

Figure 6A:
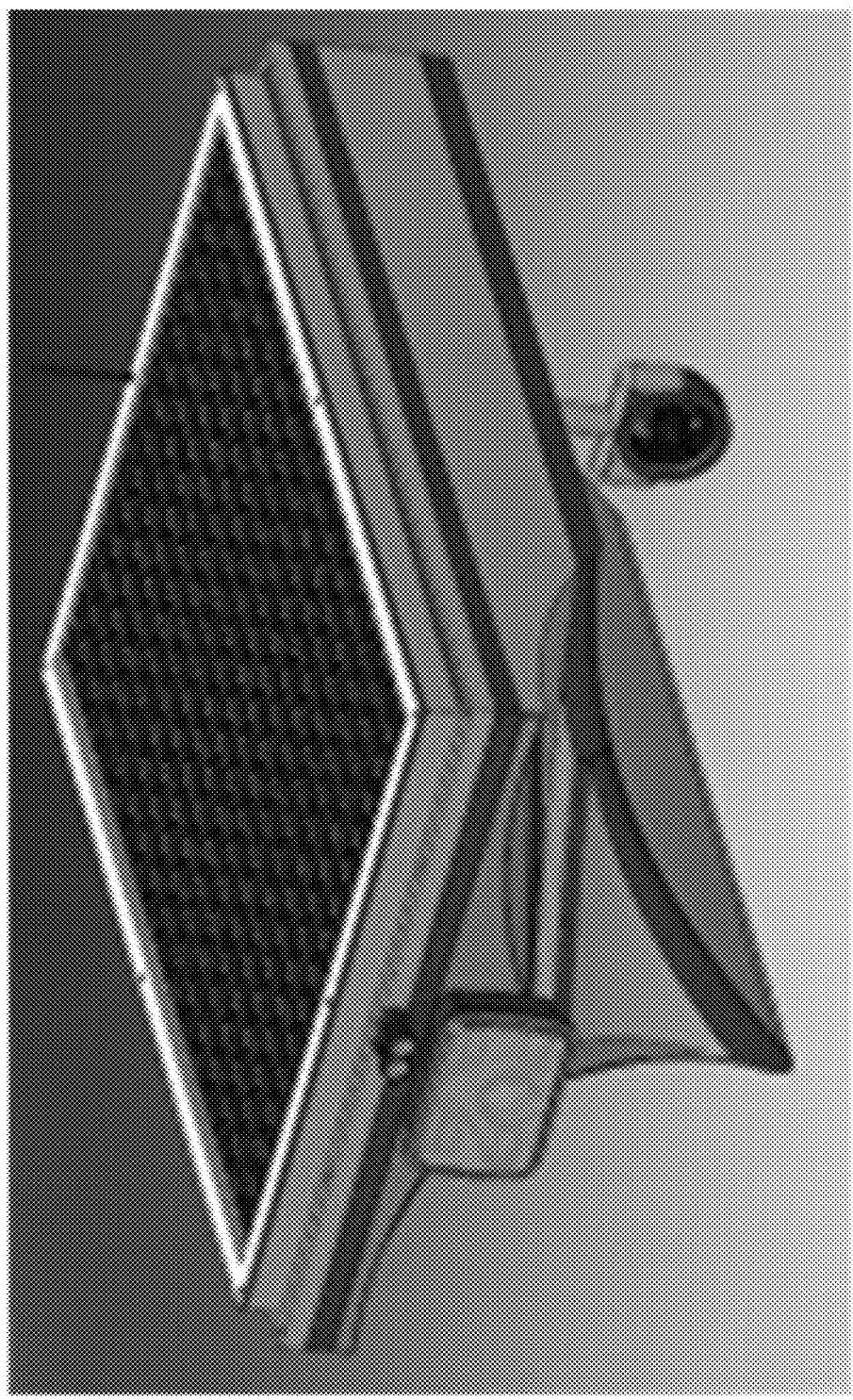
FIG. 6A-6C each illustrate views of a watercraft that can be used to detect harmful algae blooms, according to implementations of the present disclosure.
Figure 6B:
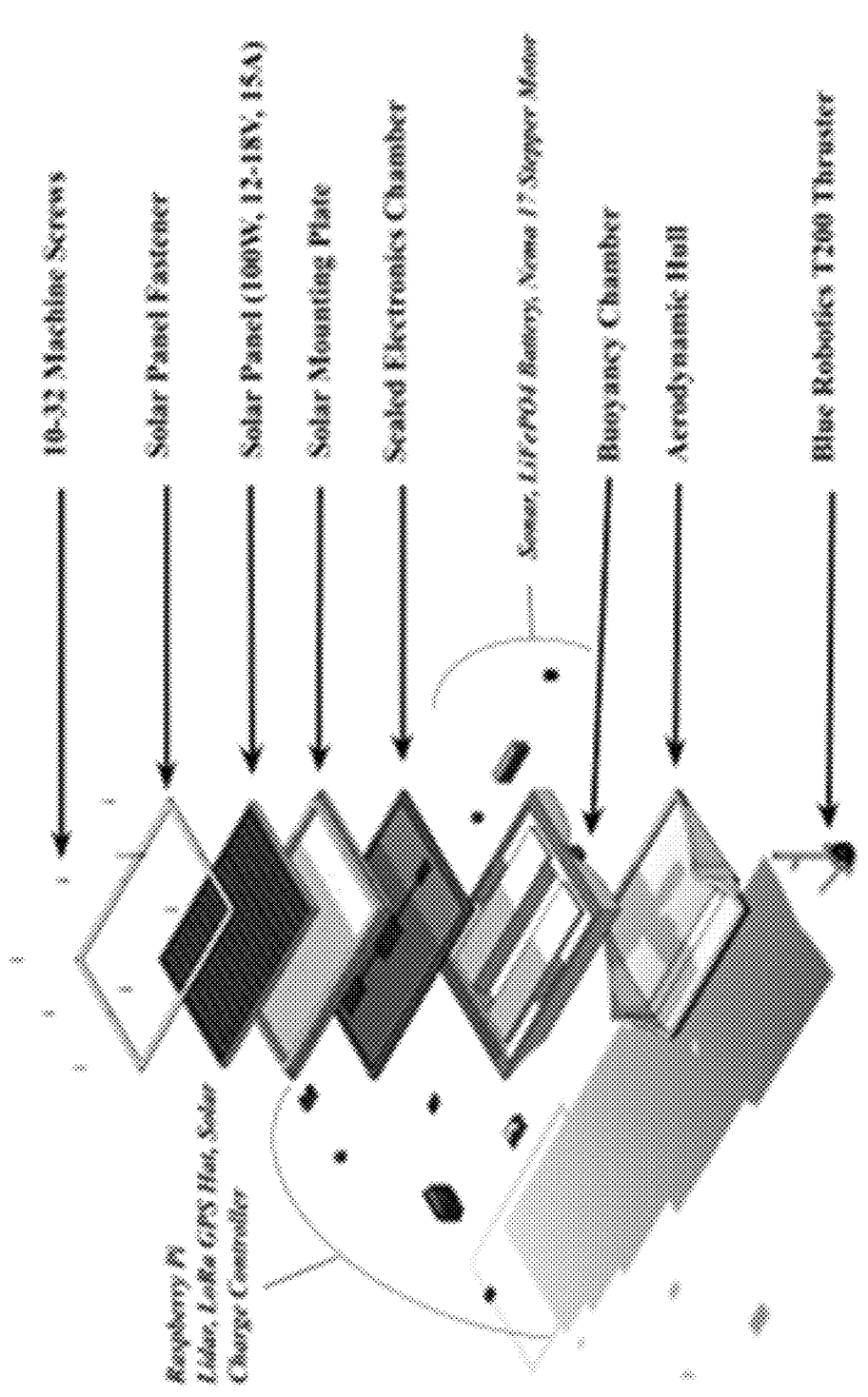

With reference to FIGS. 6A and 6B, another example implementation of an unmanned watercraft, referred to herein as "Design 2.0".

FIG. 6A illustrates a perspective view of Design 2.0, and FIG. 6B illustrates an exploded assembly view of Design 2.0. The design can include multiple layers of carbon fiber plating with interlocking channels sealed with silicone. These interlocking layers provide a complete seal between the water and interior of the drone.

A buoyancy chamber can sit toward the top of the drone and provide pockets of air around the edges of the drone. The battery, electronics, and sensors can be positioned in the direct center of the drone. This can place the center of mass of the drone near the center of the drone to reduce the likelihood that the drone capsizes.

Figure 6C:
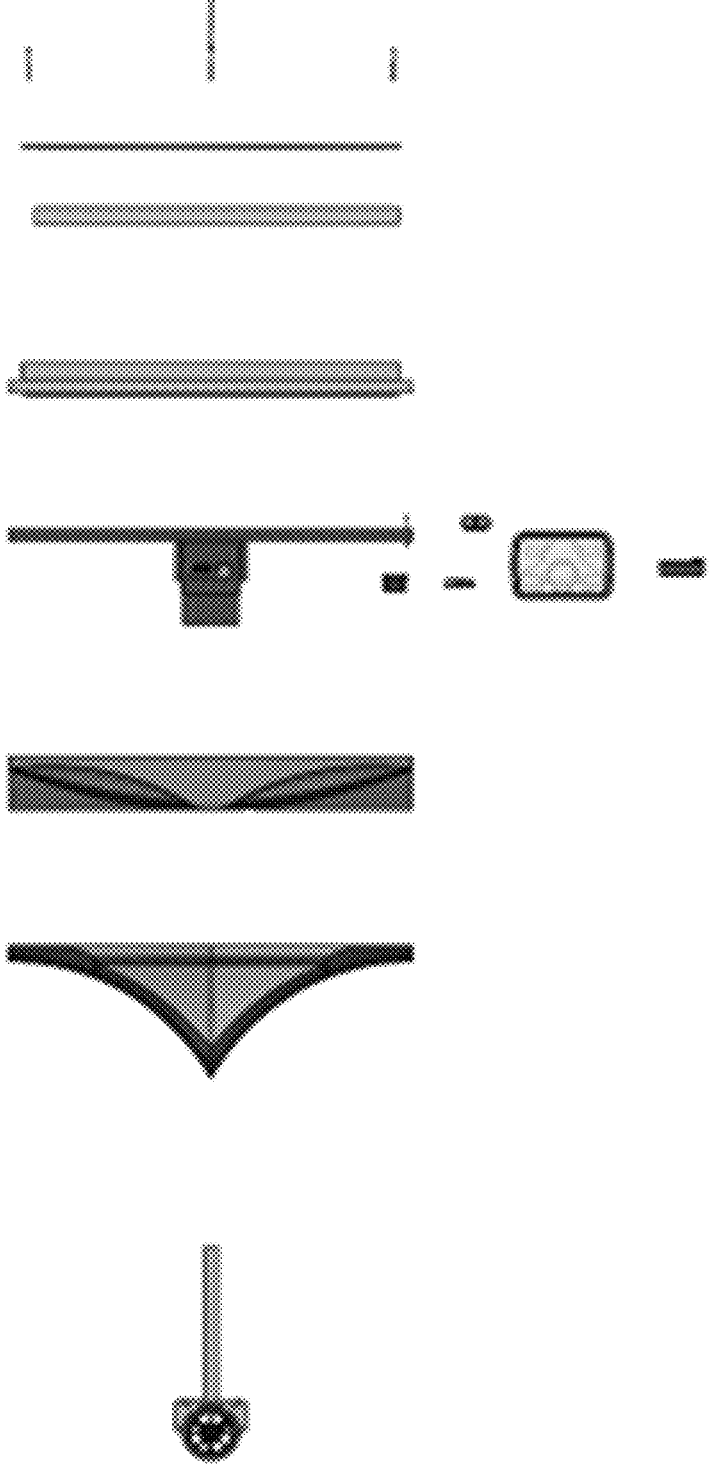

The bottom component of the drone can be formed from a single piece of molded carbon fiber. Designed to always sit below the surface of the water, the aerodynamic hull can efficiently cut through the water and reduce drag. FIG. 6C illustrates a side view of another example boat hull, including how the components can be fit together or be interlocked together to create the drone assembly.

The present disclosure contemplates that the hull can be formed using any method of boat construction or combinations of methods of boat construction. Non-limiting examples include construction techniques using cement, modeled and coated styrofoam, a waterproof box with hydrodynamic additions, 3D printed parts, fully wooden, etc. A 3D printed shape can be highly customizable.

Different designs and construction techniques can be hydrodynamic and present different tradeoffs.

Figure 7A:
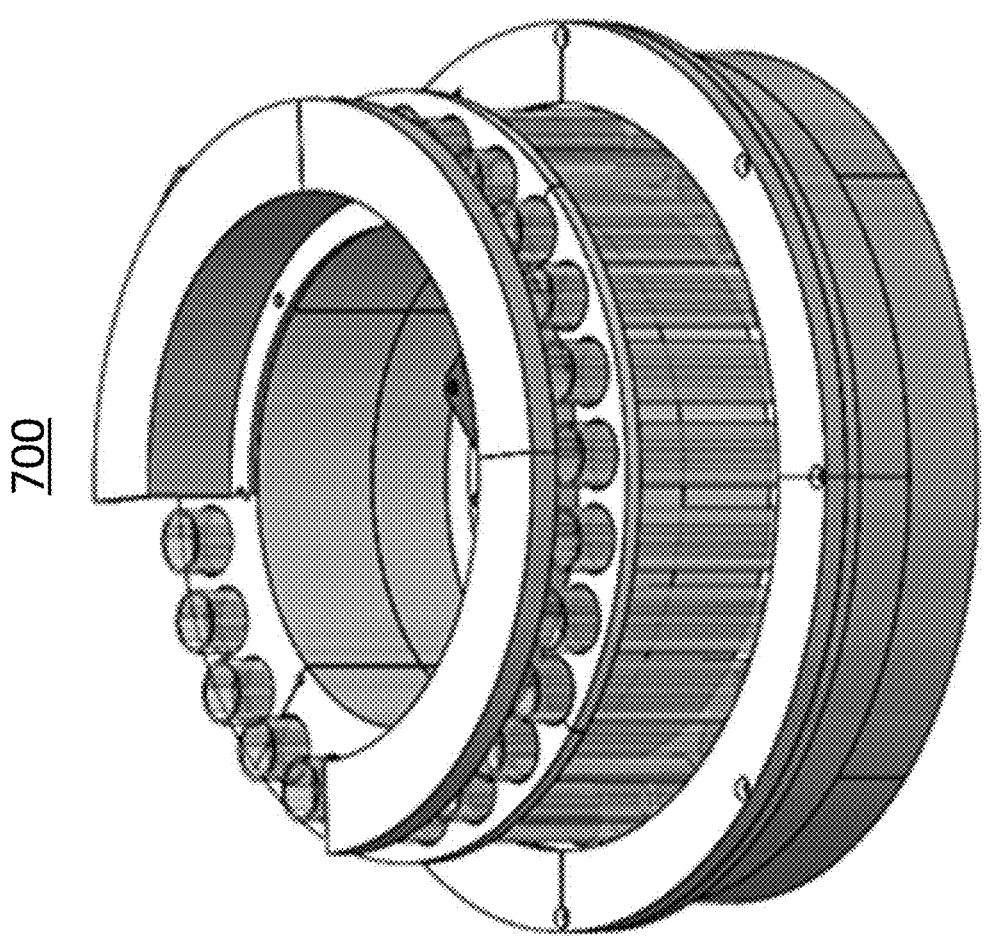
FIG. 7A illustrates a perspective view of a test tube carousel configured to hold 24 test tubes, according to implementations of the present disclosure.
Figure 7B:
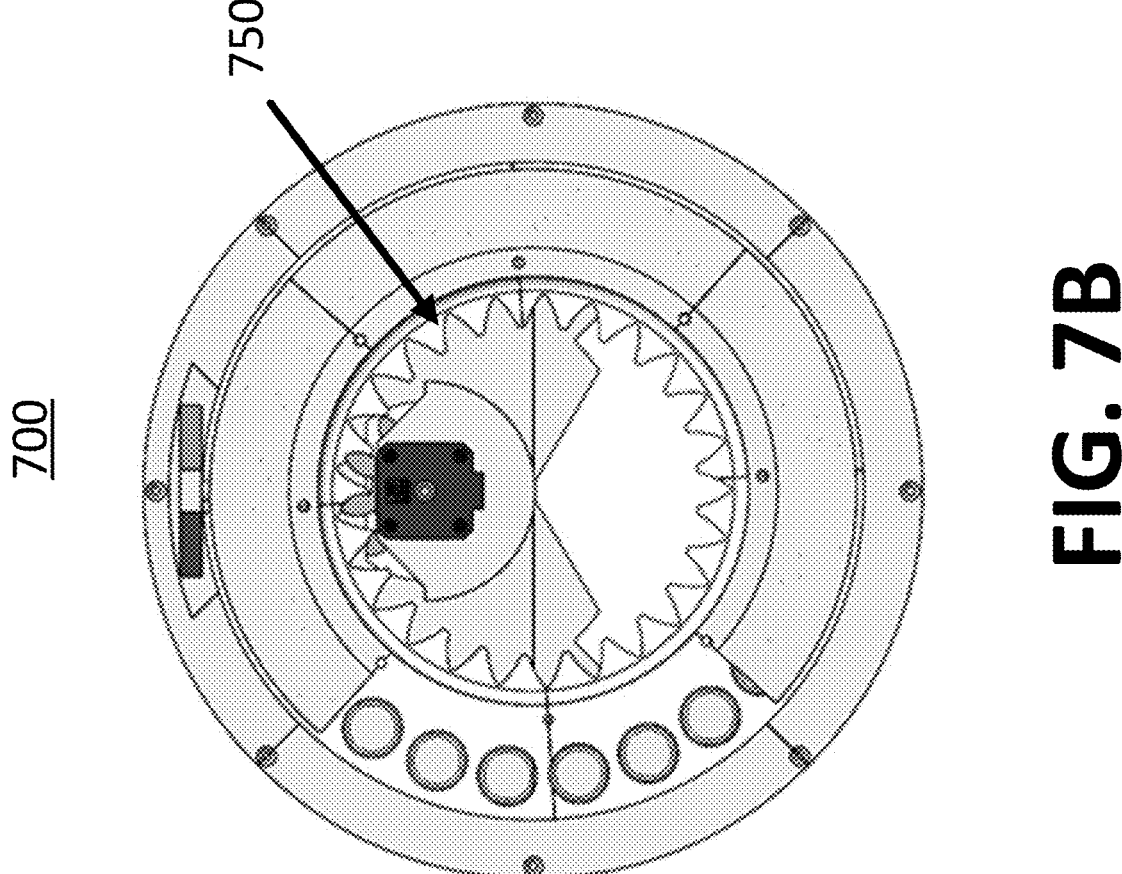
FIG. 7B illustrates a bottom view of the test tube carousel illustrated in FIG. 7A.

Another example implementation of the present disclosure described herein includes a test tube carousel 700, illustrated with reference to FIG. 7A and FIG. 7B. FIG. 7A illustrates a perspective view of the test tube carousel 700. The test tube carousel can be connected to a pump and tube system (not shown) that feeds water from the outside environment into a test tube. The test tube carousel 700 can have gear teeth 750, shown in FIG. 7B, that rotate the test tube carousel to move each test tube one position over. There is also a divot 760 on the bottom base 770 of the carousel (also shown in FIG. 7E). When a test tube passes over the divot, it can drop into the divot and expose the top of the test tube so that it can be filled with water.

Test tube carousels according to the design shown in FIGS. 7A-7F can include any number of test tubes, for example, in the example implementation shown in FIG. 7A, the carousel has 24 test tubes. In another example implementation, the test tube carousel 790 was significantly decreased in size from the previous carousel design. The test tube carousel 790 shown in FIGS. 7C-D includes 12 test tubes. Changing the number and/or size of the test tubes can allow for the design of the hull to be changed. For example, the test tube carousel 790 with only 12 test tubes can minimize material usage and reduce 3D printing time for both the test tube carousel and the hull.

Figure 7C:
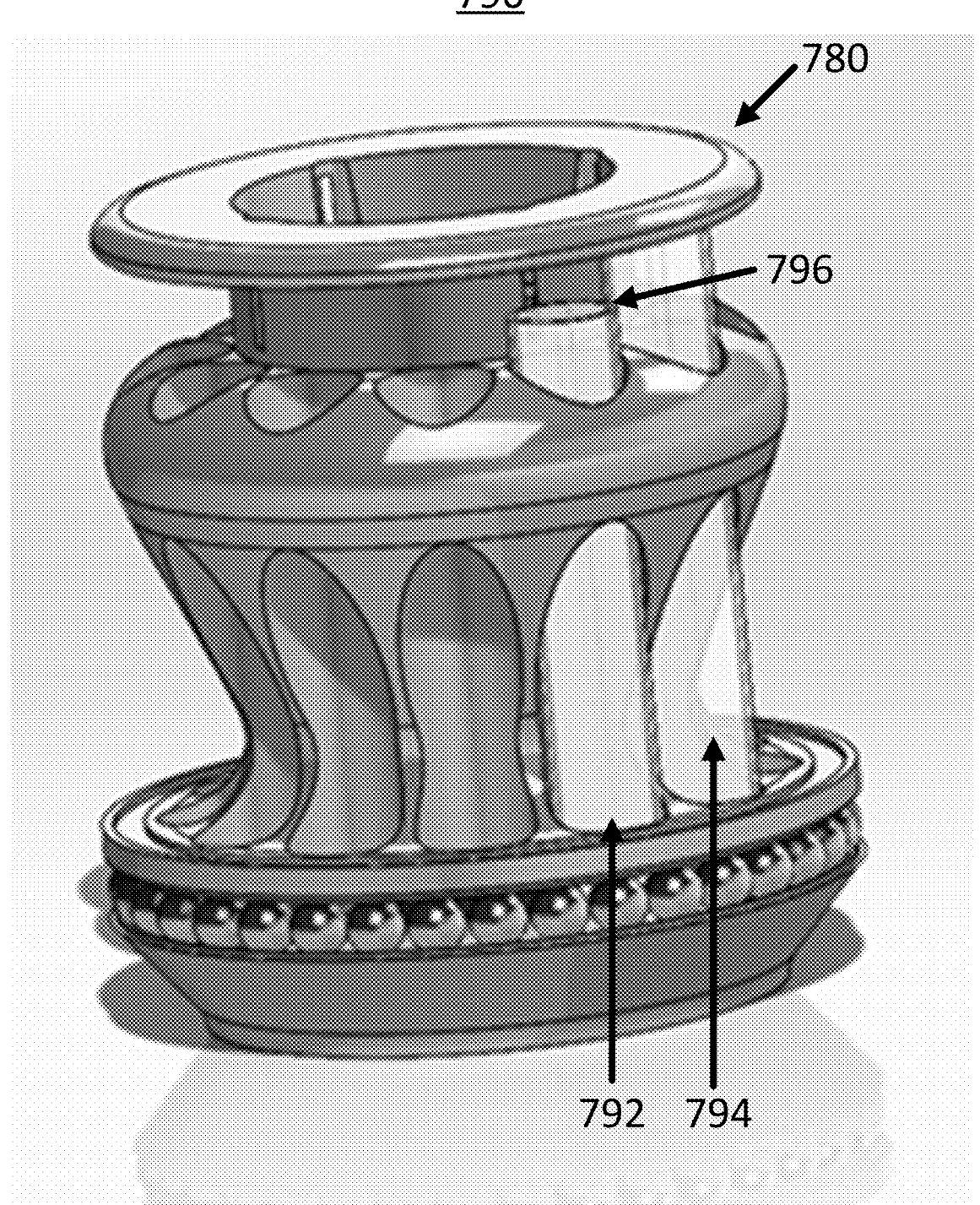
FIGS. 7C and 7D each illustrate a perspective view of a test tube carousel configured to hold 12 test tubes, according to implementations of the present disclosure.
Figure 7D:
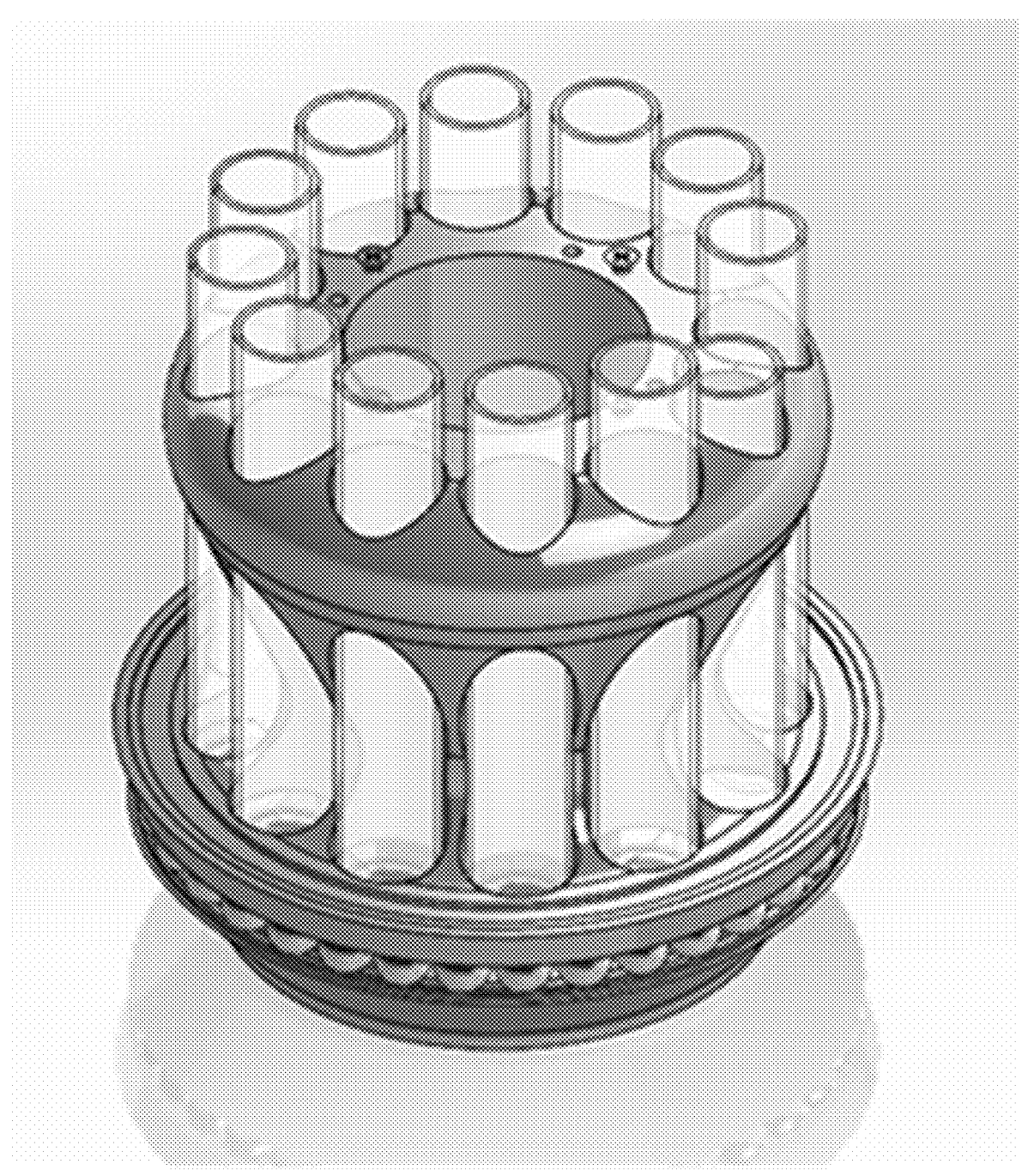
Figure 7E:
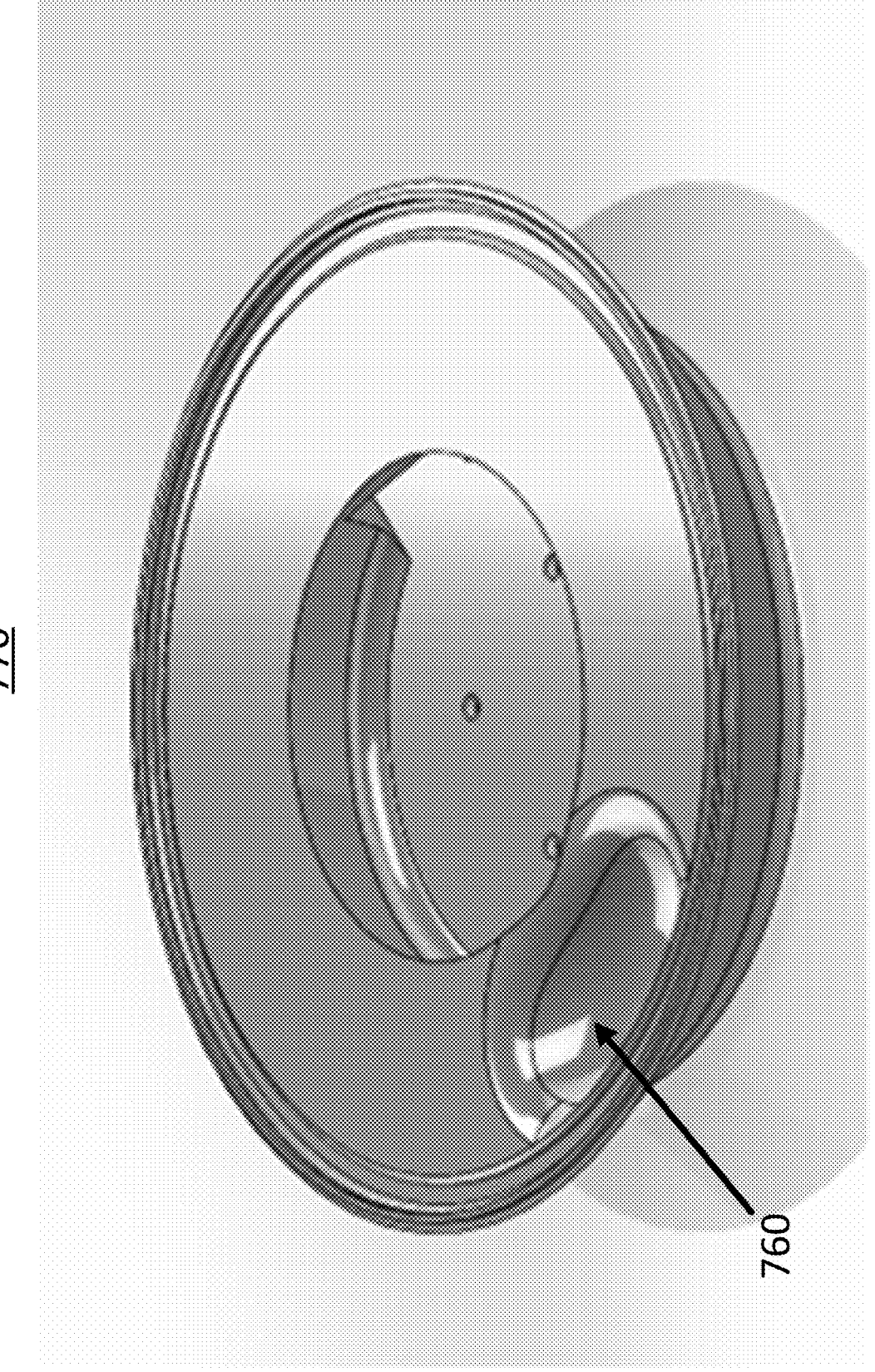
FIG. 7E illustrates a base with a divot, that can be used as a base for the test tube carousel illustrated in FIGS. 7C and 7D.

As shown in FIG. 7C, a cap 780 with a rubber lining can be screwed onto the test tube carousel 790 and the cap 780 can apply enough force for the tubes to seal and but still be able to rotate. As shown in FIG. 7C, the tube 792 in the divot is below the cap 780 and the mouth 796 of the tube 792 is exposed so it can be filled, and the tube 794 outside the divot is sealed against the cap 780.

Figure 7F:
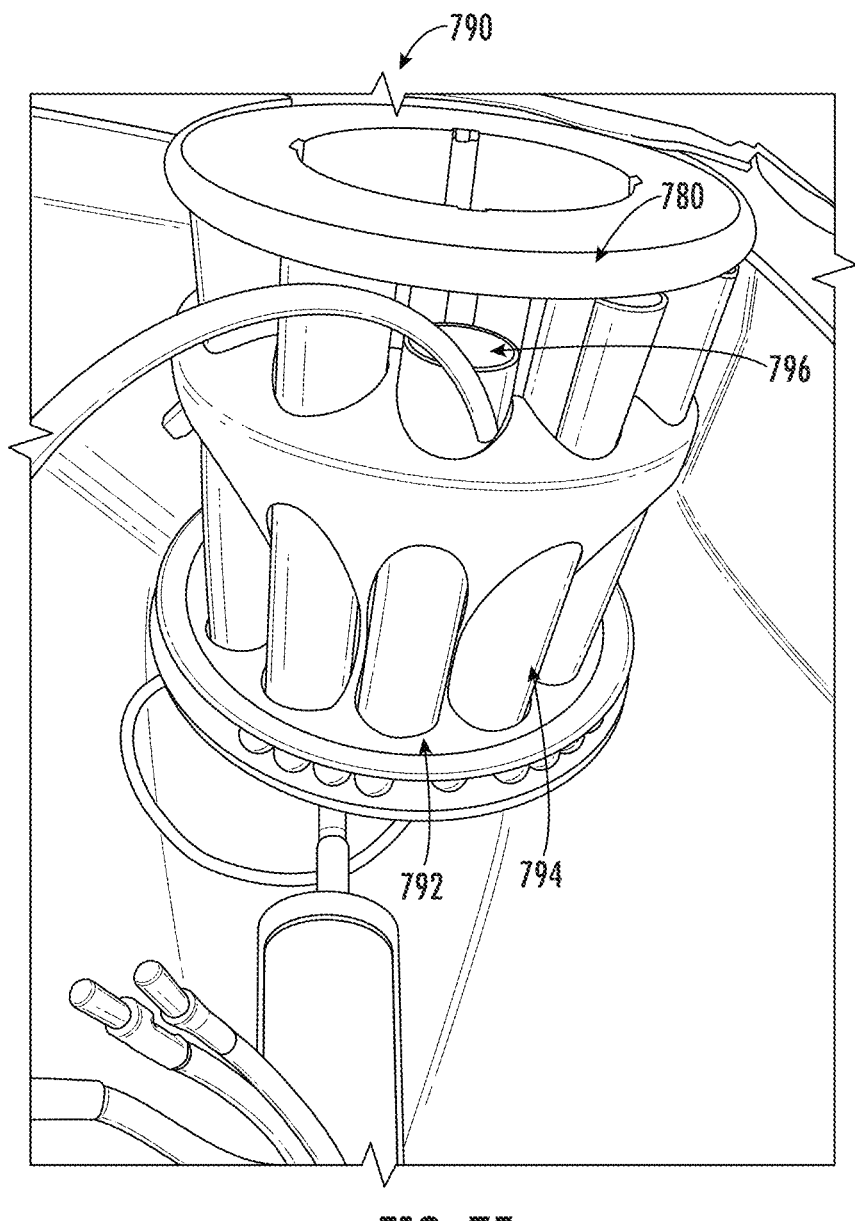
FIG. 7F illustrates a test tube carousel with 12 test tubes that was 3D printed and positioned in a watercraft hull, according to an implementation of the present disclosure.

The test tube carousel 700 can collect water for the microPAD portion of the sensing while the SCMS sensor can directly stick out of the boat and collect data without any assistance. A 3D printed example implementation of a test tube carousel 790 is illustrated in FIG. 7F. A tube 798 is positioned to fill the test tube 792 in the divot (not shown).

With reference to FIG. 8A-11I, additional example hull designs are described herein that can be used with some implementations of the present disclosure.

Figure 8A:
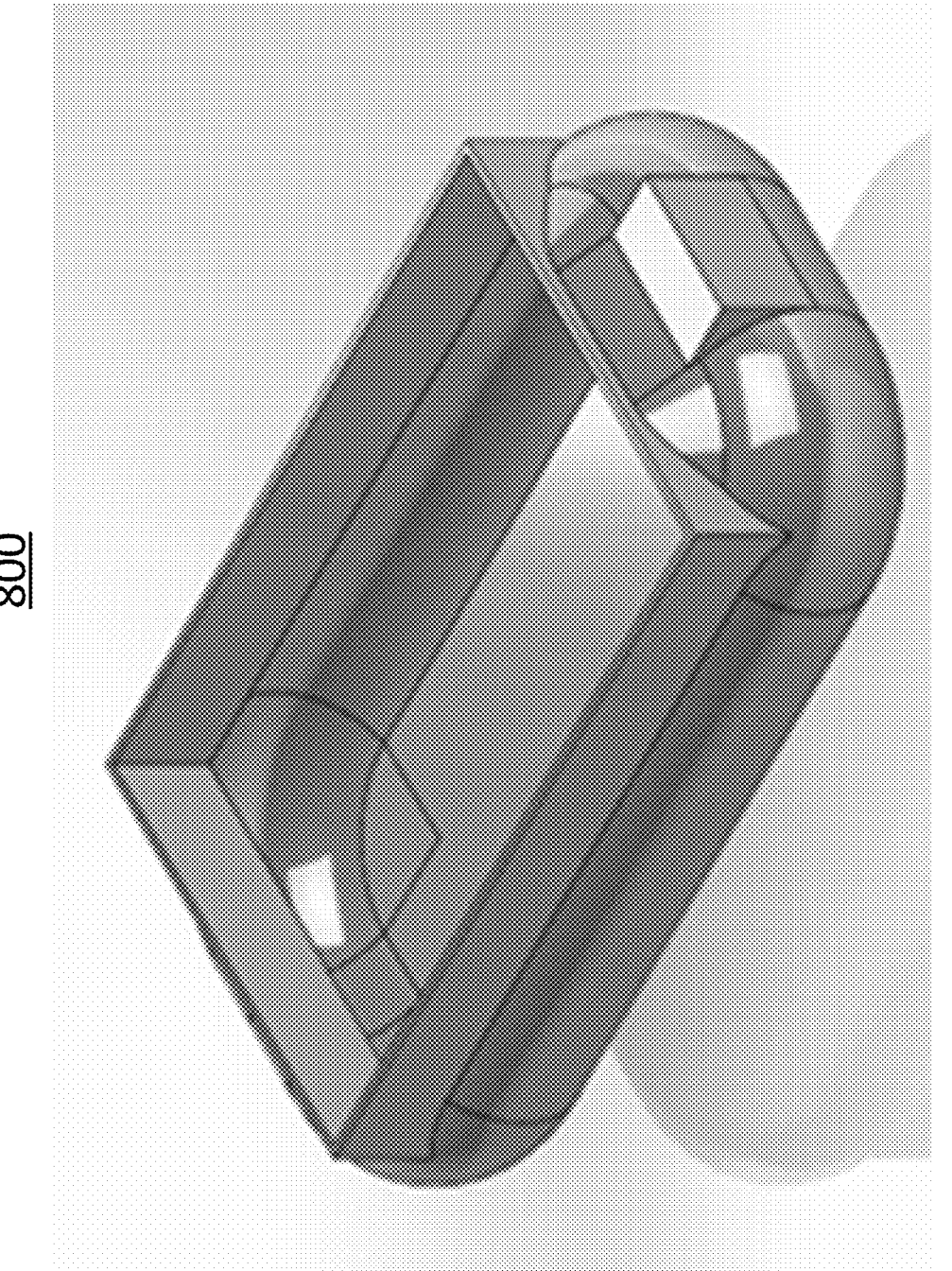
FIG. 8A-8C each illustrate perspective views of an implementation of a watercraft that can be used in implementations of the present disclosure.

FIG. 8A illustrates a hull 800 configured to fit the size of the solar panel and test tube carousel (not shown). The hull 800 has a flat bottom and very round edges. The harsh corners can be difficult to 3D print.

Figure 8B:
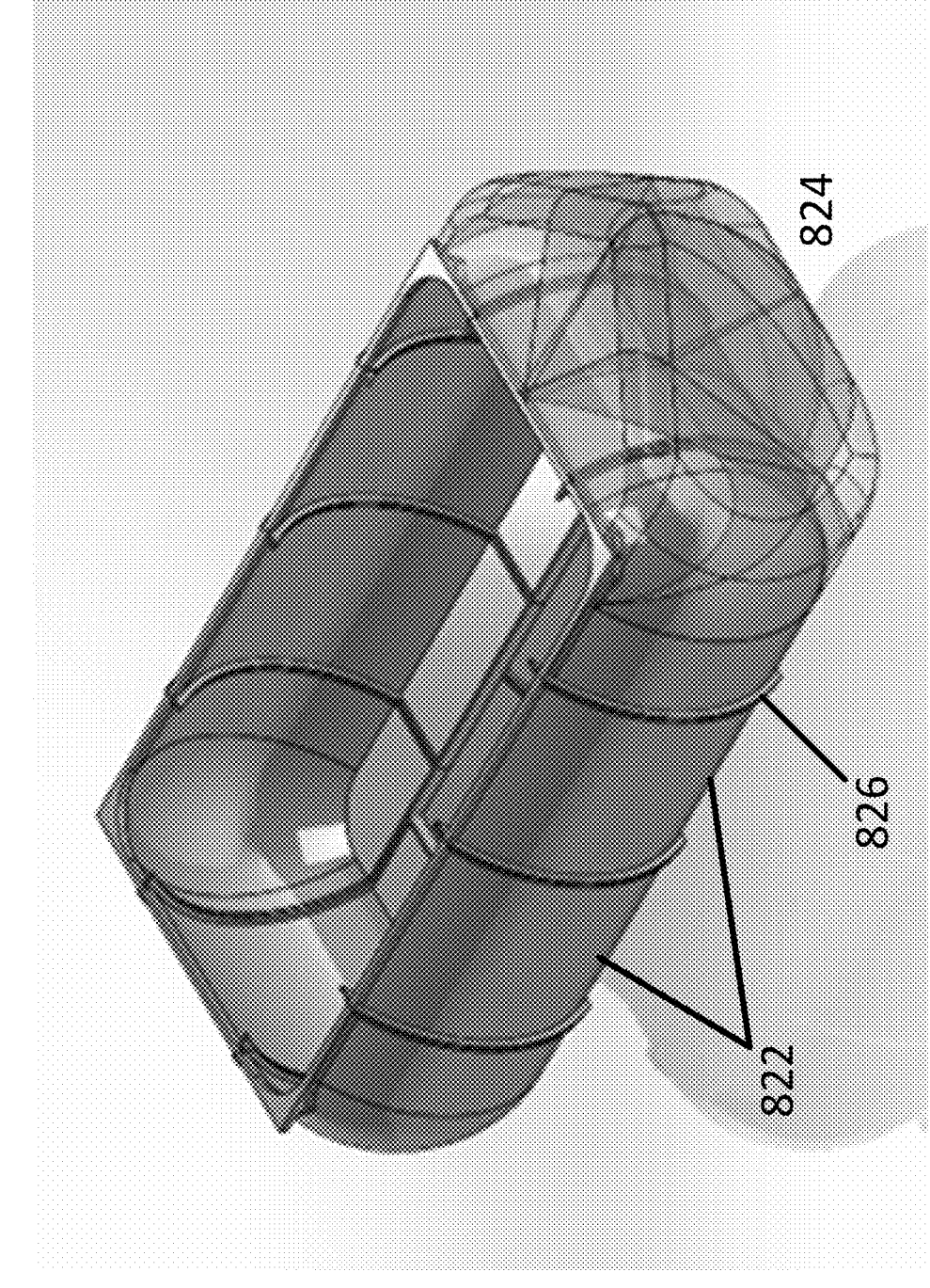

FIG. 8B illustrates another hull 820 that can be sectioned for 3D printing and assembly. The hull 820 is made of shapes 822, and the shapes 822 have a simpler geometry and ridges 826 are present on the outside to make gluing the pieces together easier with the use of clamps. Additionally, a curved nose 824 was added to allow the boat to better travel over waves. It is still mostly flat on the bottom until the very front at the curved nose 824.

Figure 8C:
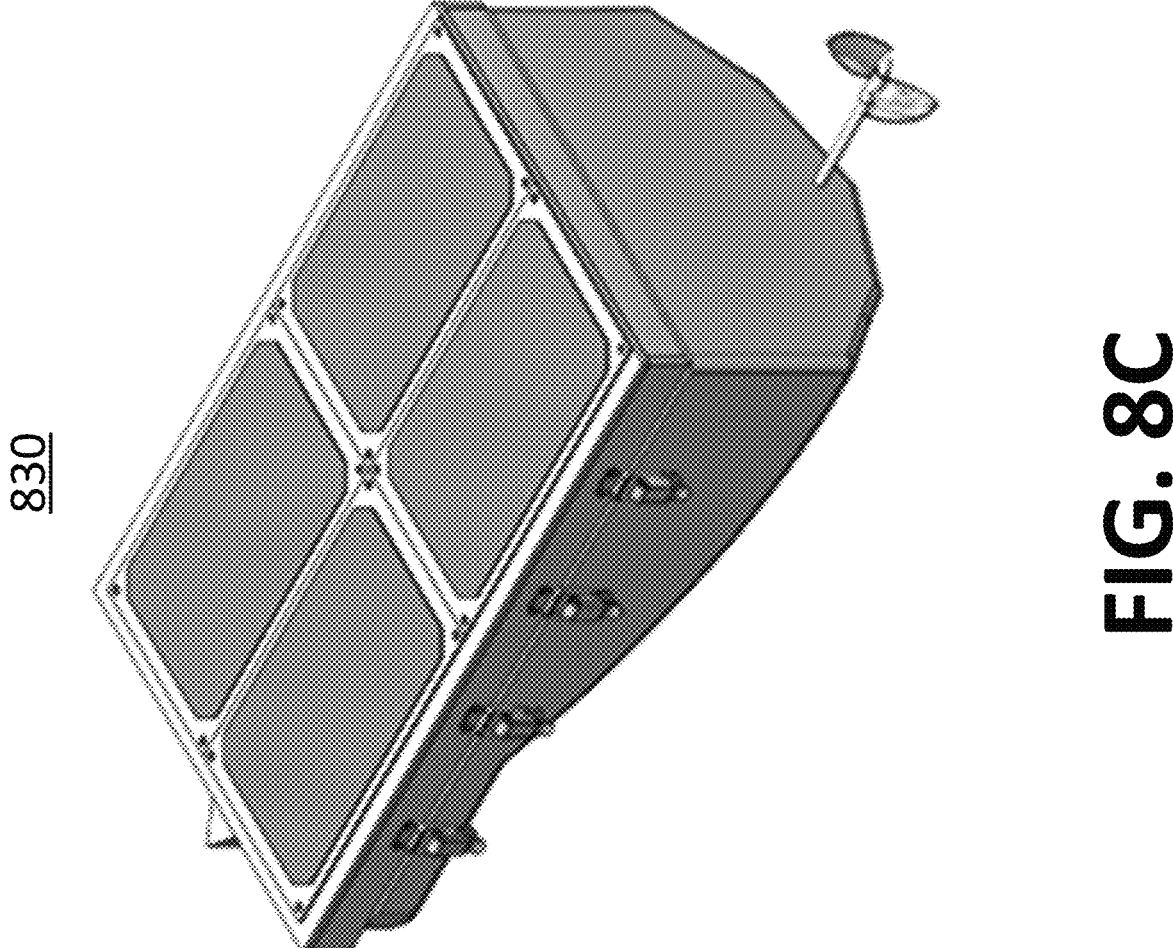

FIG. 8C illustrates a perspective view of another hull 830. The hull 830 includes the curved nose 824 from FIG. 8B (not shown) and elongates it for better hydrodynamics. It uses the same sectioned pieces (not shown) and ridges (not shown) for assembly illustrated in FIG. 8B. The ridges and pieces are not visible in FIG. 8C because FIG. 8C is an illustration of the hull after final assembly and sanding.

Figure 9A:
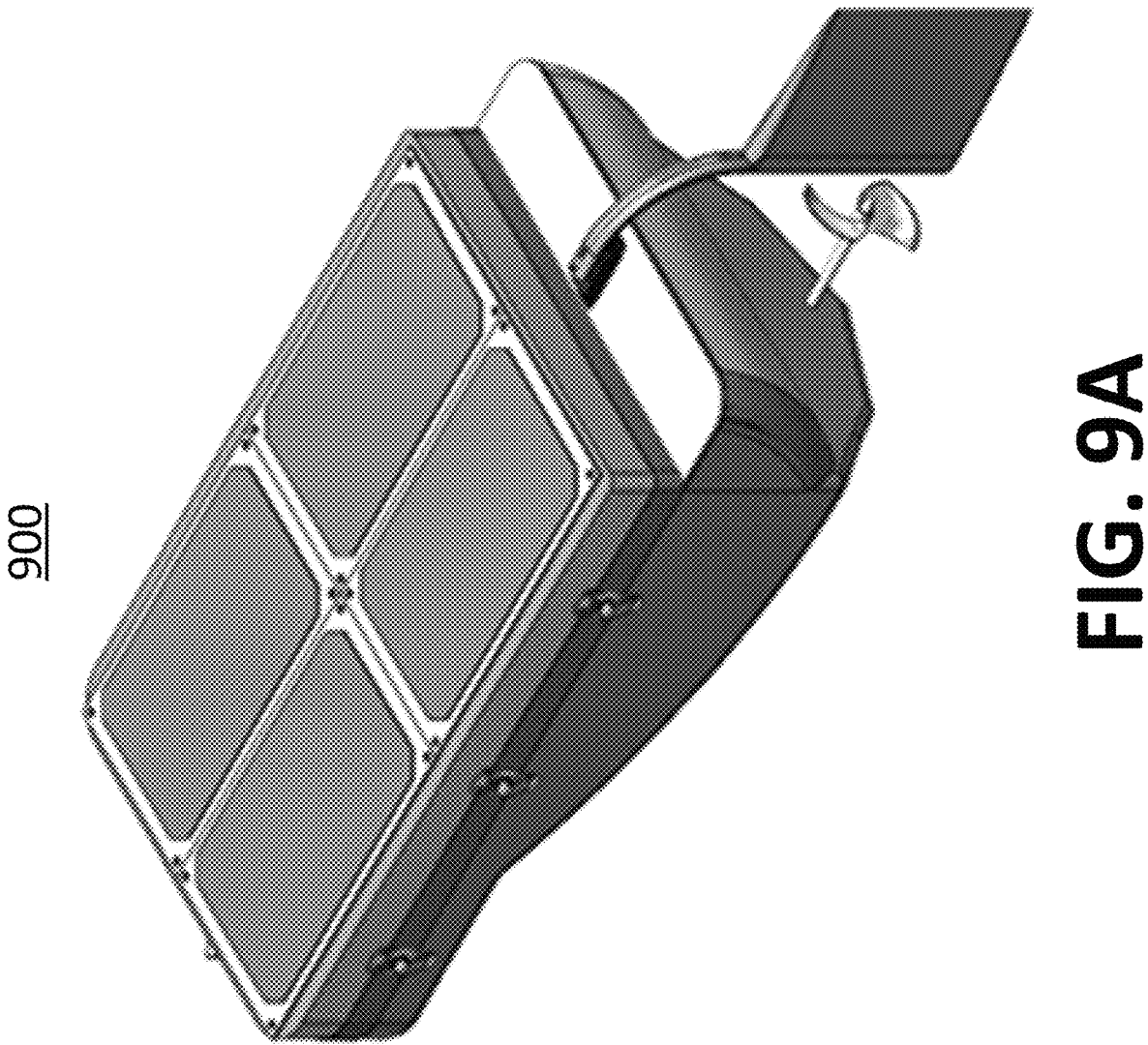
FIG. 9A illustrates a perspective view of a watercraft, according to an implementation of the present disclosure.
Figure 9B:
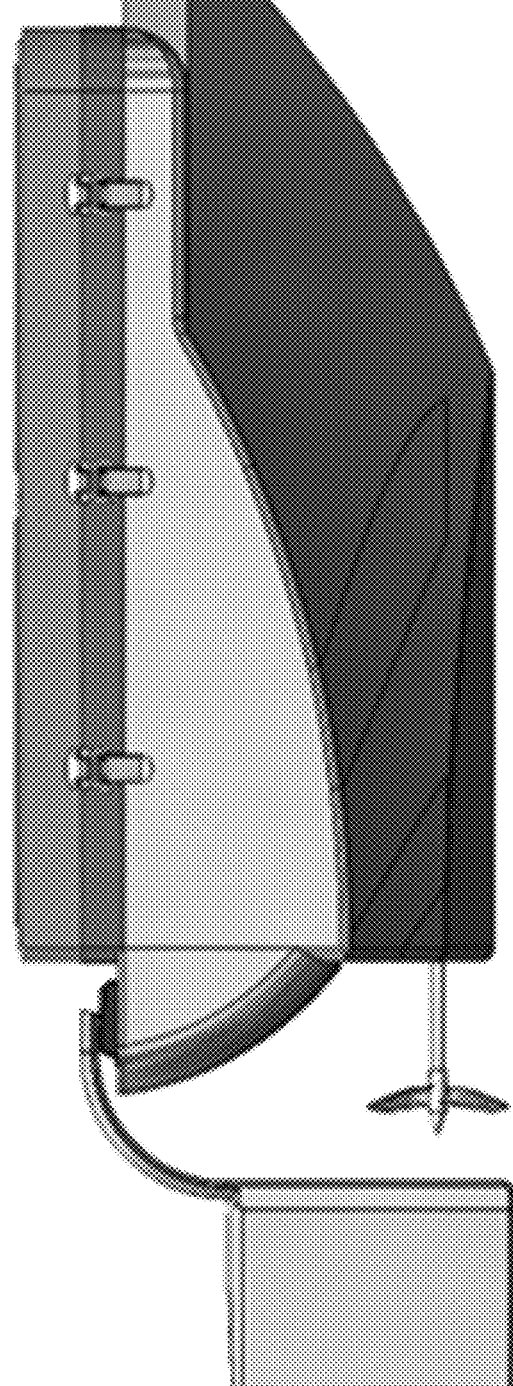
FIG. 9B illustrates a side view of the watercraft illustrated in FIG. 9A.
Figure 9C:
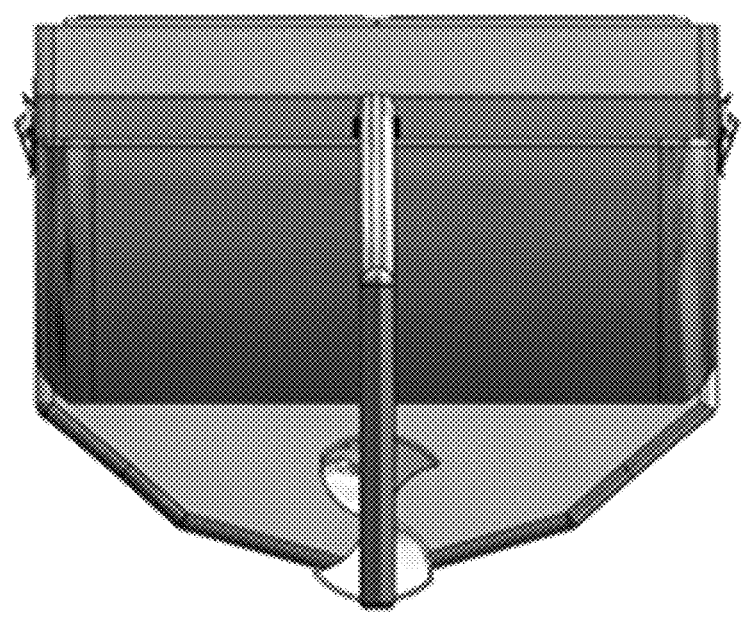
FIG. 9C illustrates a rear view of the watercraft illustrated in FIG. 9A.
Figure 9D:
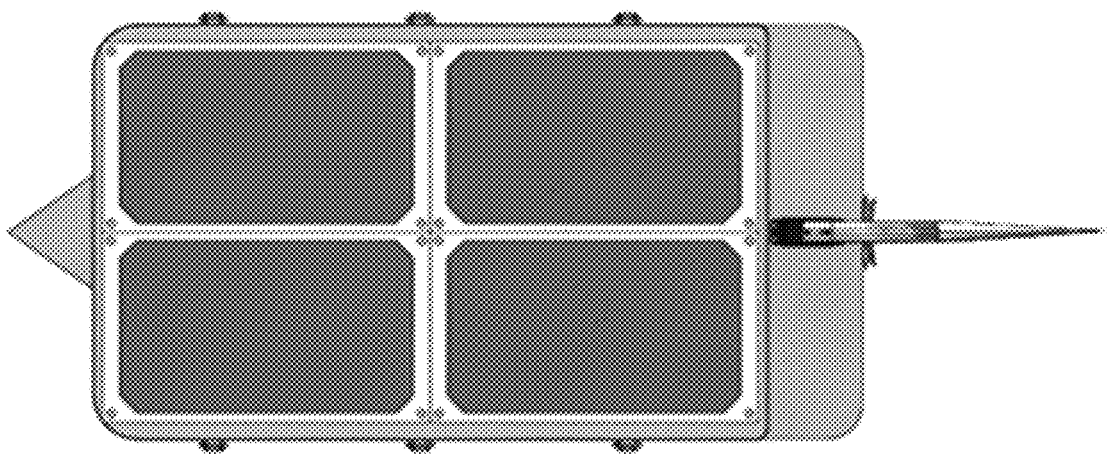
FIG. 9D illustrates a top view of the watercraft illustrated in FIG. 9A.

Another example implementation of an autonomous water-borne drone 900 is shown in FIGS. 9A-9F. The example implementation includes a preliminary sensor, secondary sensor (microPAD), water collection, autonomous navigation, and one thruster. The design includes an improved back shape and additional storage space. The hull size is also decreased from earlier designs as the carousel is redesigned to have a smaller size. FIGS. 9A-9D illustrate views of an example watercraft, where FIG. 9A illustrates a perspective view of a watercraft, FIG. 9B illustrates a side view of the watercraft, FIG. 9C illustrates a rear view of the watercraft, and FIG. 9D illustrates a top view of the watercraft.

Figure 9E:
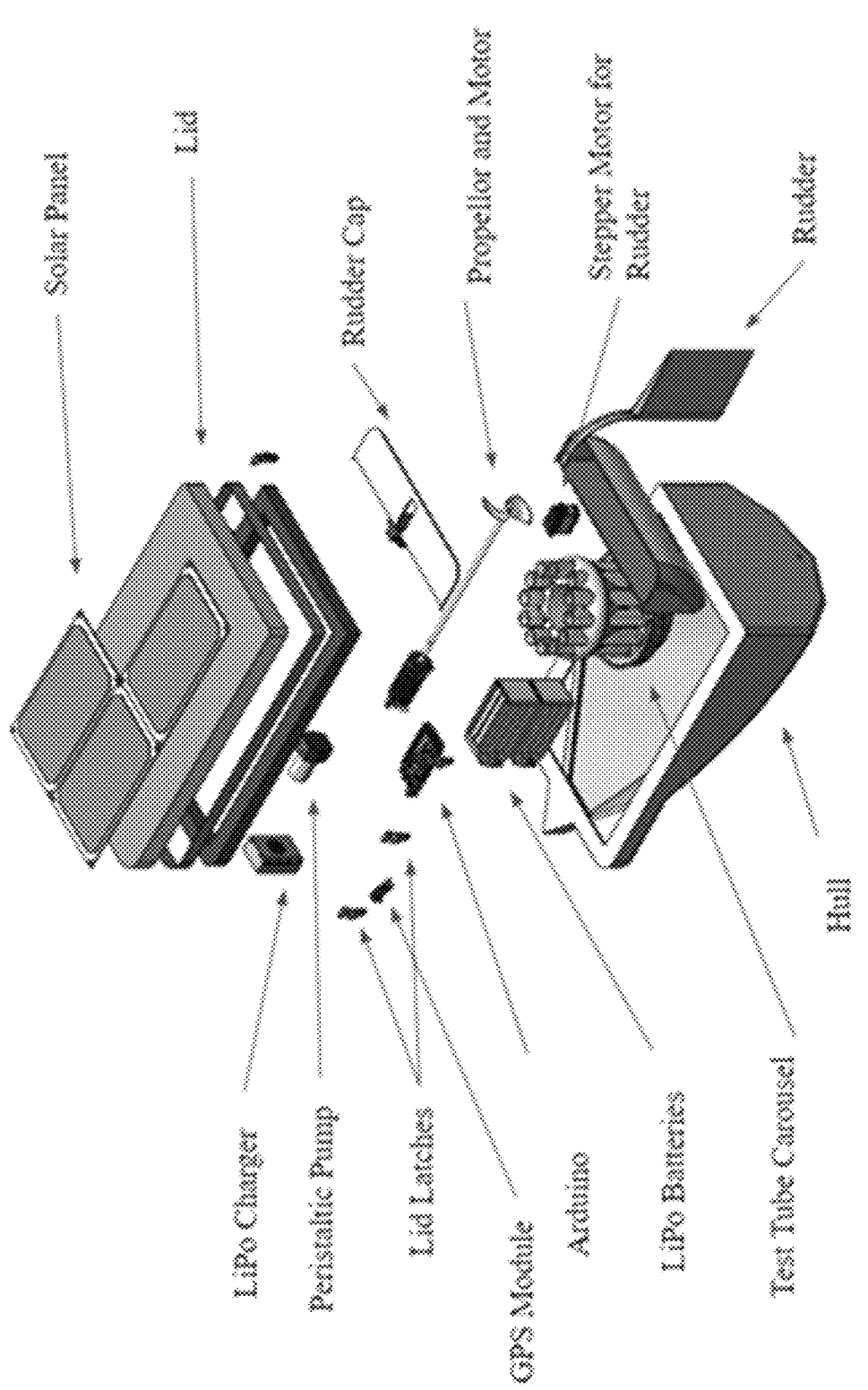
FIG. 9E illustrates an exploded perspective view of the watercraft illustrated in FIG. 9A.
Figure 9F:
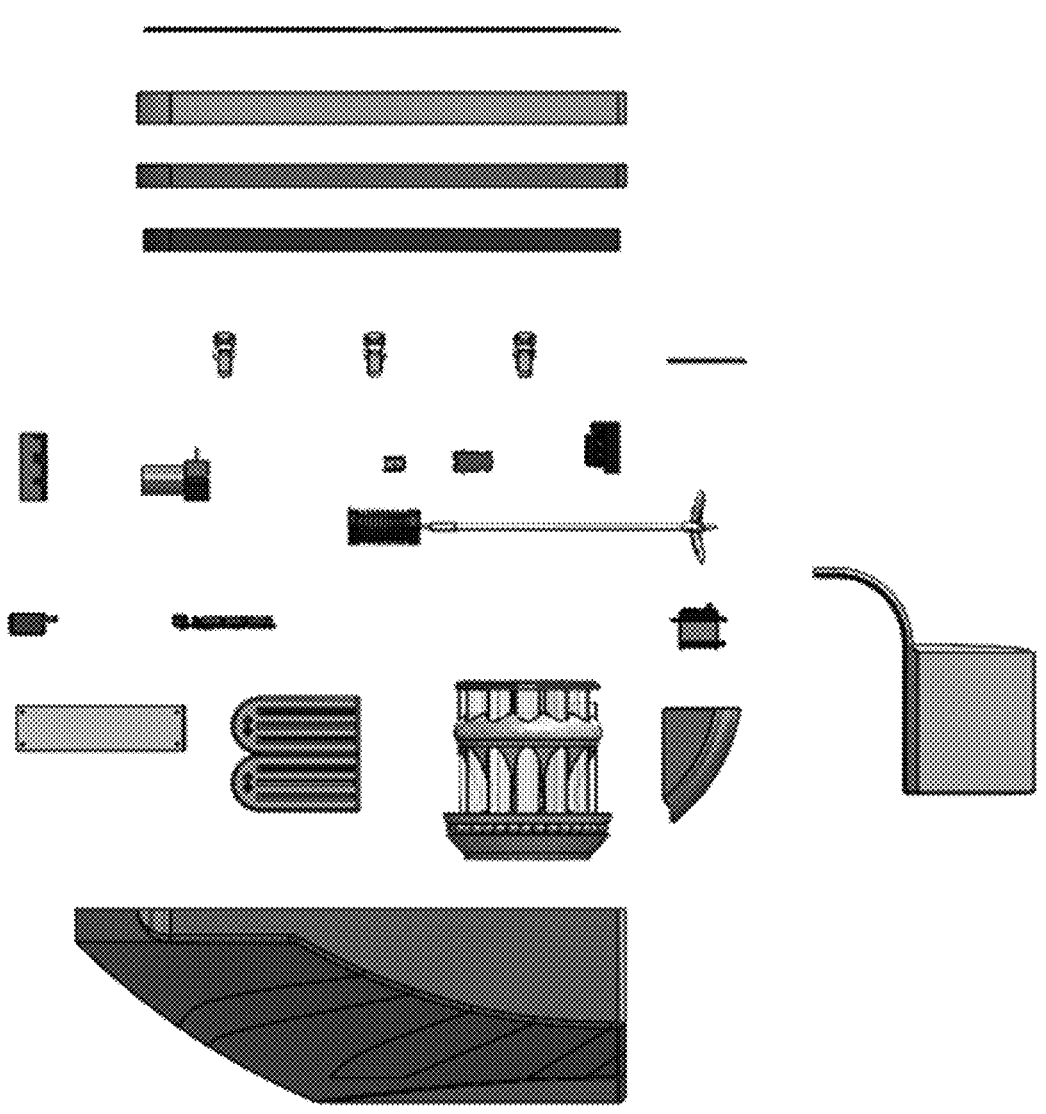
FIG. 9F illustrates an exploded side view of the watercraft illustrated in FIG. 9A.

FIG. 9E and FIG. 9F show exploded views of another example implementation of the drone and how the internal components can be arranged. The waterproof hull is filled with the test tube carousel, pump, microcontroller, and batteries. The microcontroller includes code configured to operate and control the thruster, rudder, and carousel. In the example implementation described with reference to FIGS. 9E and 9F, the microcontroller is an Arduino microcontroller, but it should be understood that the microcontroller can be any computing device, e.g., the computing device 1200 illustrated and described with respect to FIG. 12.

Figure 10:
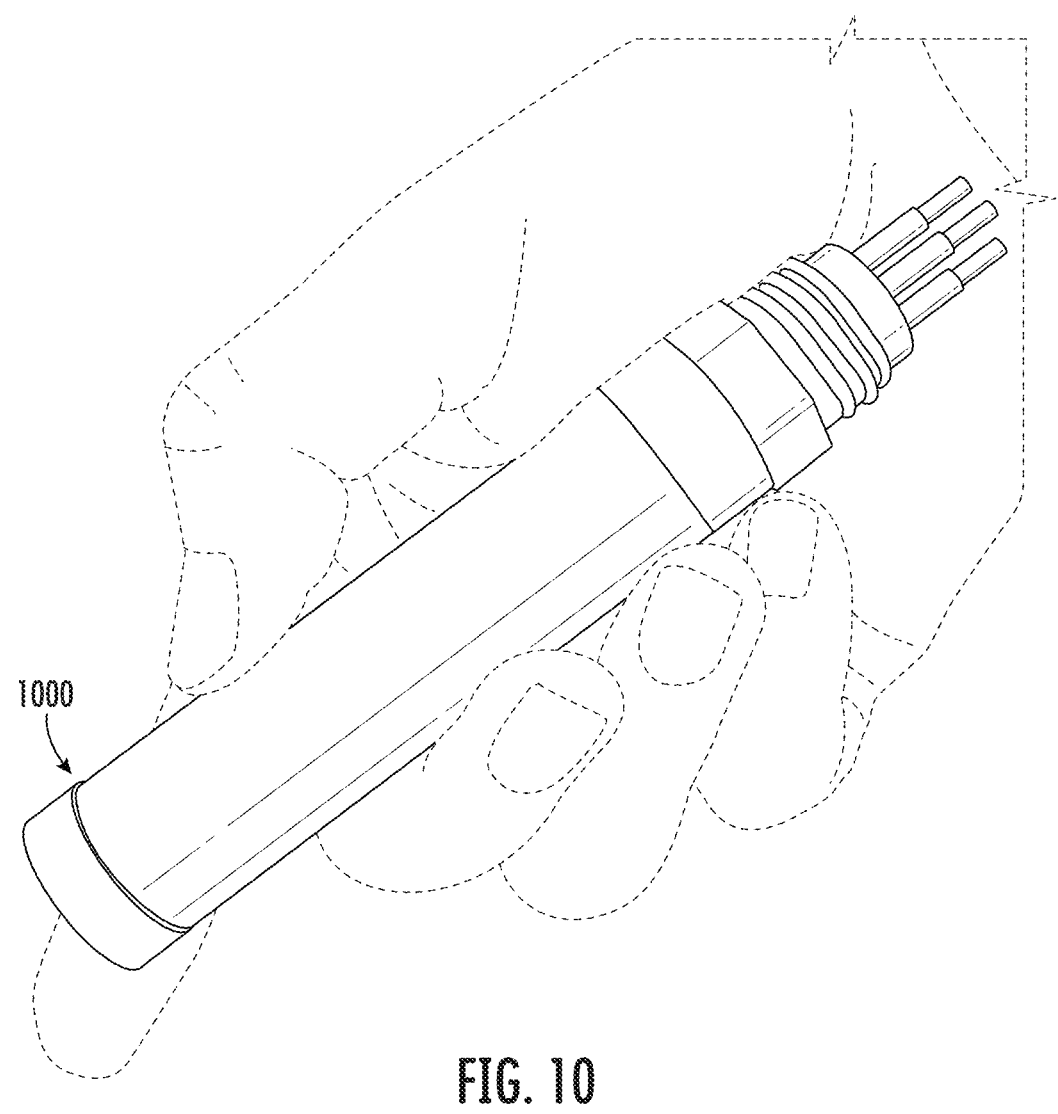
FIG. 10 illustrates a C-Fluor sensor that can be used in implementations of the present disclosure.

An SCMS sensor can identify algae, but may not be capable of identifying the toxins found within HABS. As an example, the SCMS sensor can identify algae through chlorophyll and phycocyanin concentrations. In the example implementation of the present disclosure, a C-Flor Submersible Probe sensor 1000 was used, as shown in FIG. 10. The C-Flor Submersible probe sensor can operate with low input power and analog output.

Another non-limiting example of a sensor that can be used in some implementations of the present disclosure is an electronic microPAD that can test for toxins and differentiate between HABs and regular algal blooms. A technician can use the test tubes stored in the carousel as a water source for these tests. Additionally, since the water is already contained in the tubes it would be possible to take them back to a lab if the microPAD testing is inconclusive.

Figure 11A:
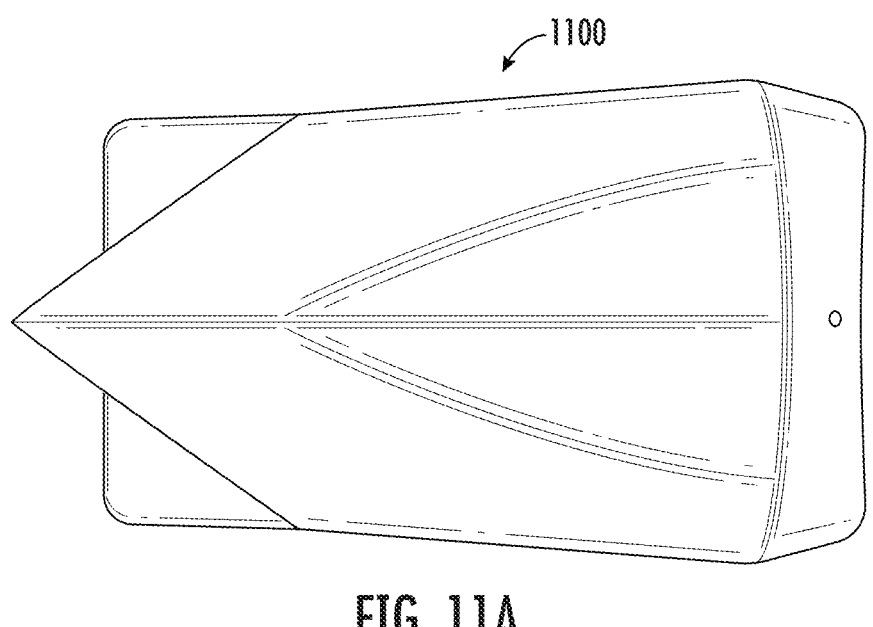
FIGS. 11A-11I each illustrate views of a watercraft that was constructed, according to implementations of the present disclosure.
Figure 11B:
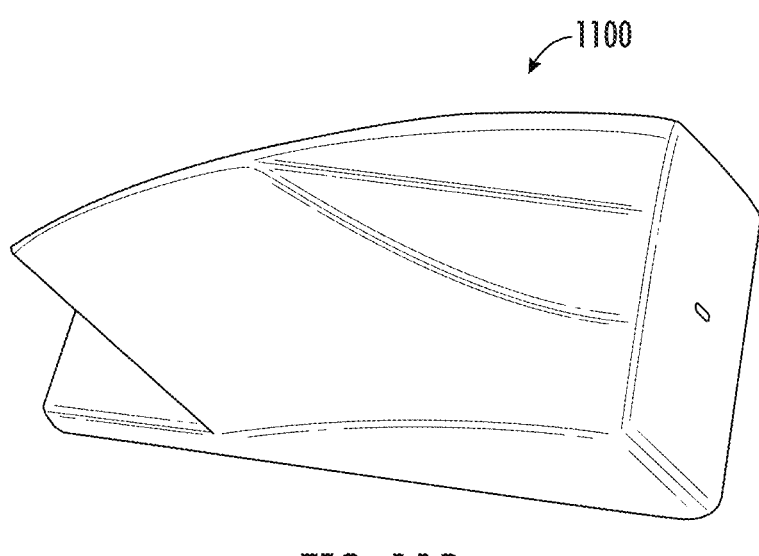

FIG. 11A illustrates an example of a sanded hull 1100 formed by combining separate 3D printed pieces and gluing them together. Power sanders can be used to remove imperfections in the surface. FIG. 11B illustrates the sanded hull shown in FIG. 11A, where waterproof spray paint and primer has been applied over multiple coats to protect the hull and internal components from the body of water it is placed in.

Figure 11C:
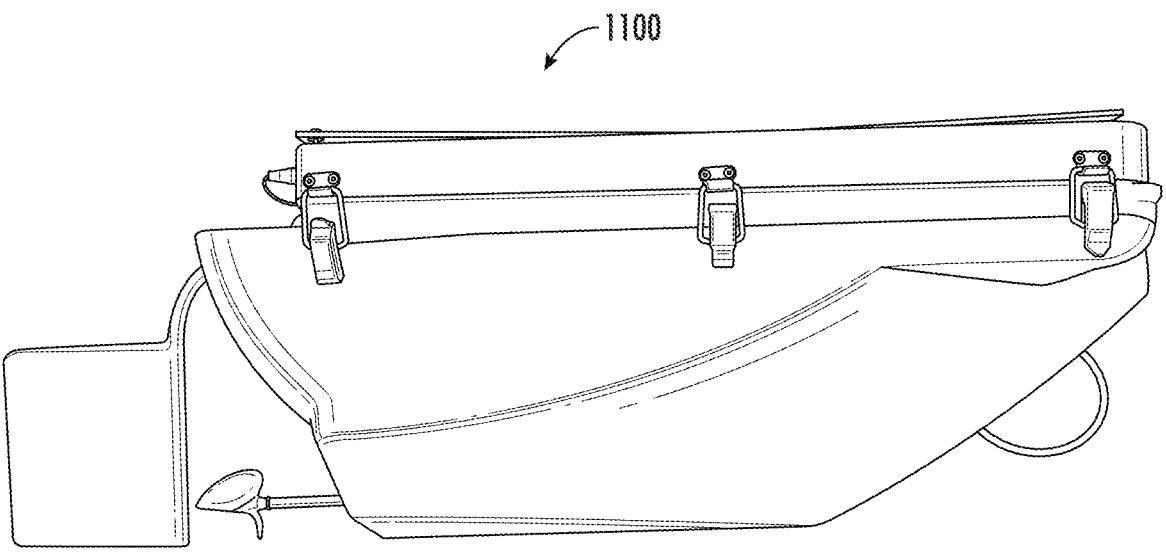
Figure 11D:
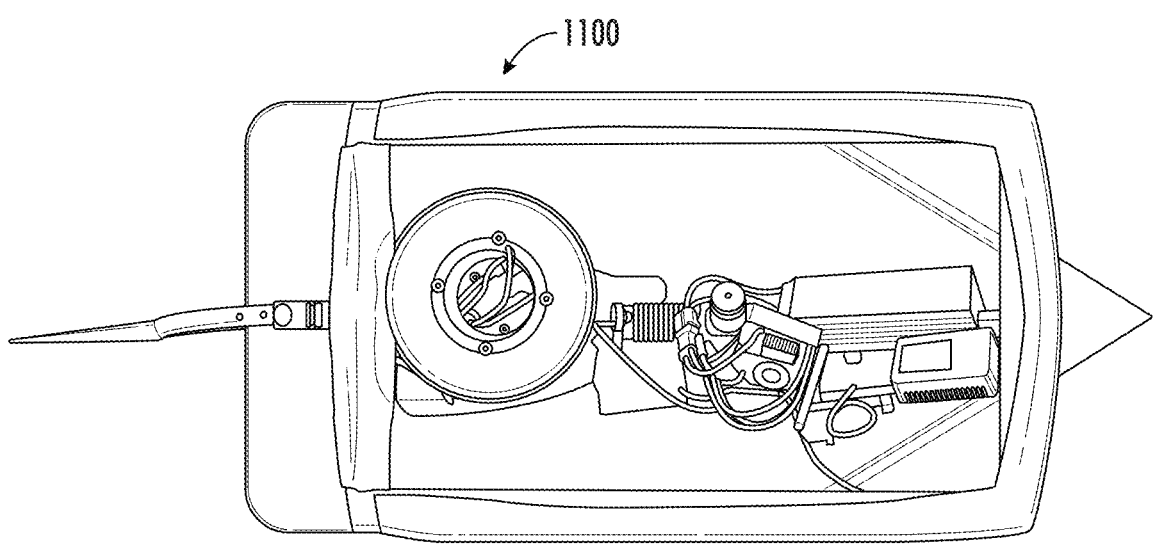
Figure 11E:
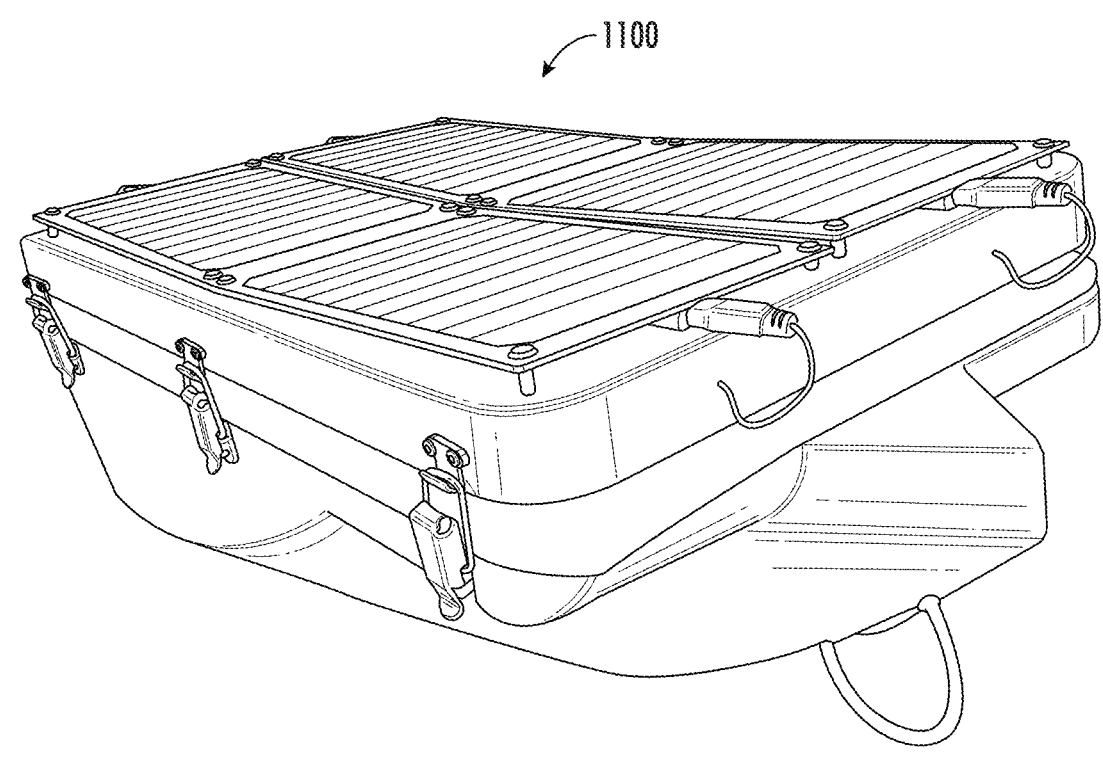
Figure 11F:
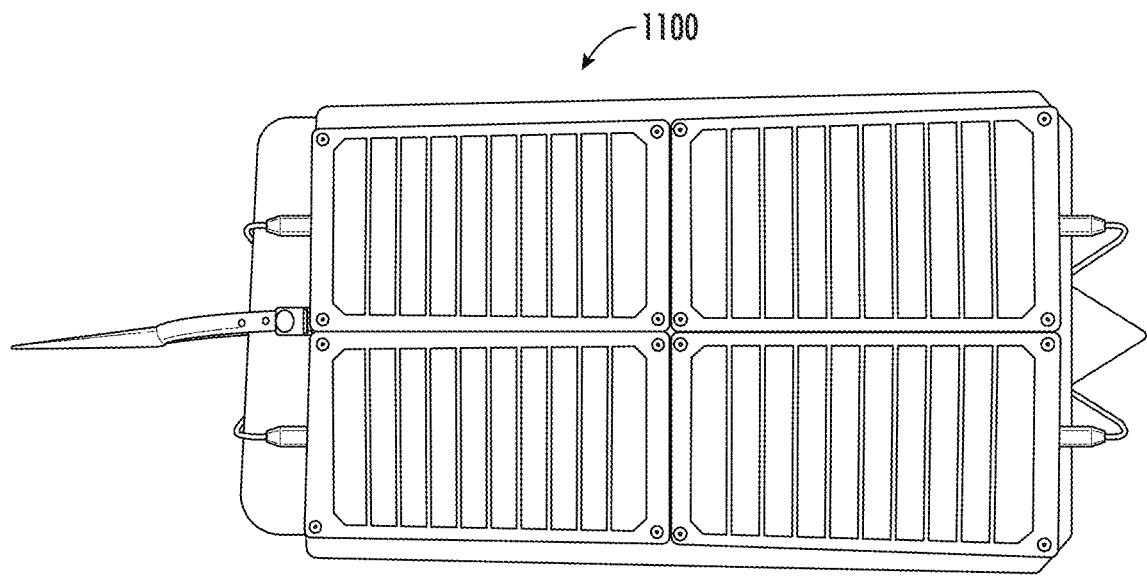
Figure 11G:
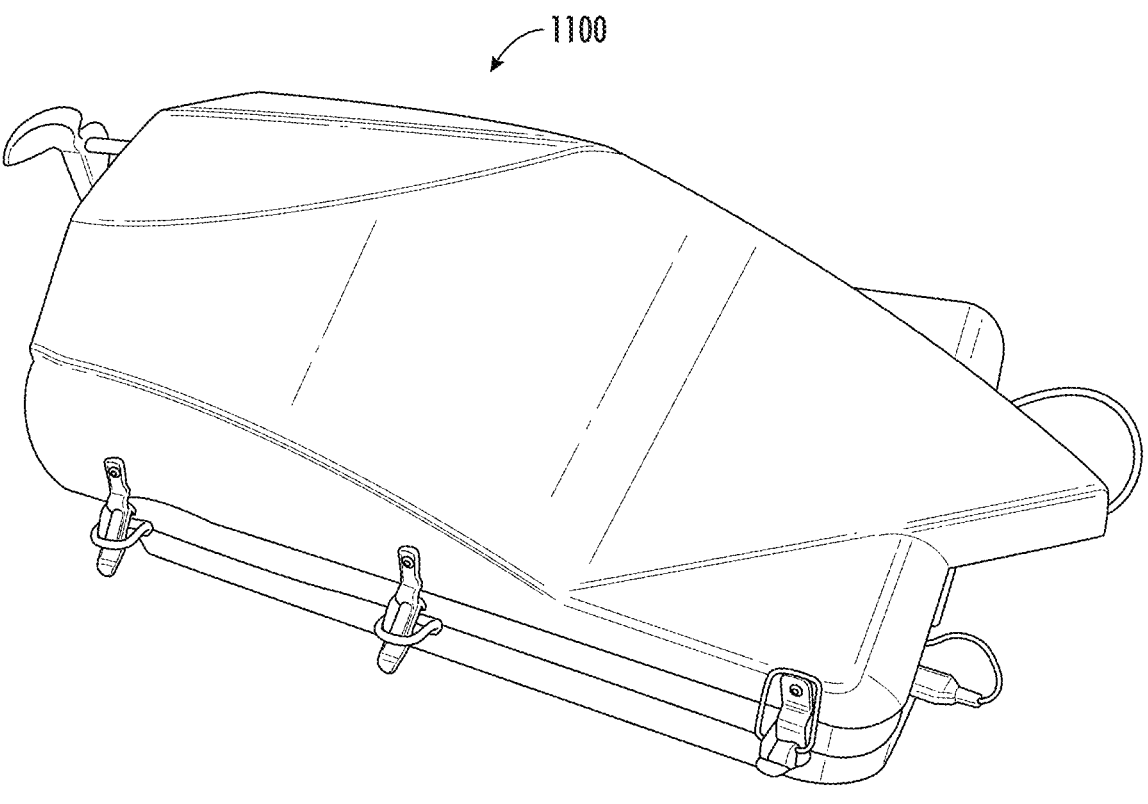
Figure 11H:
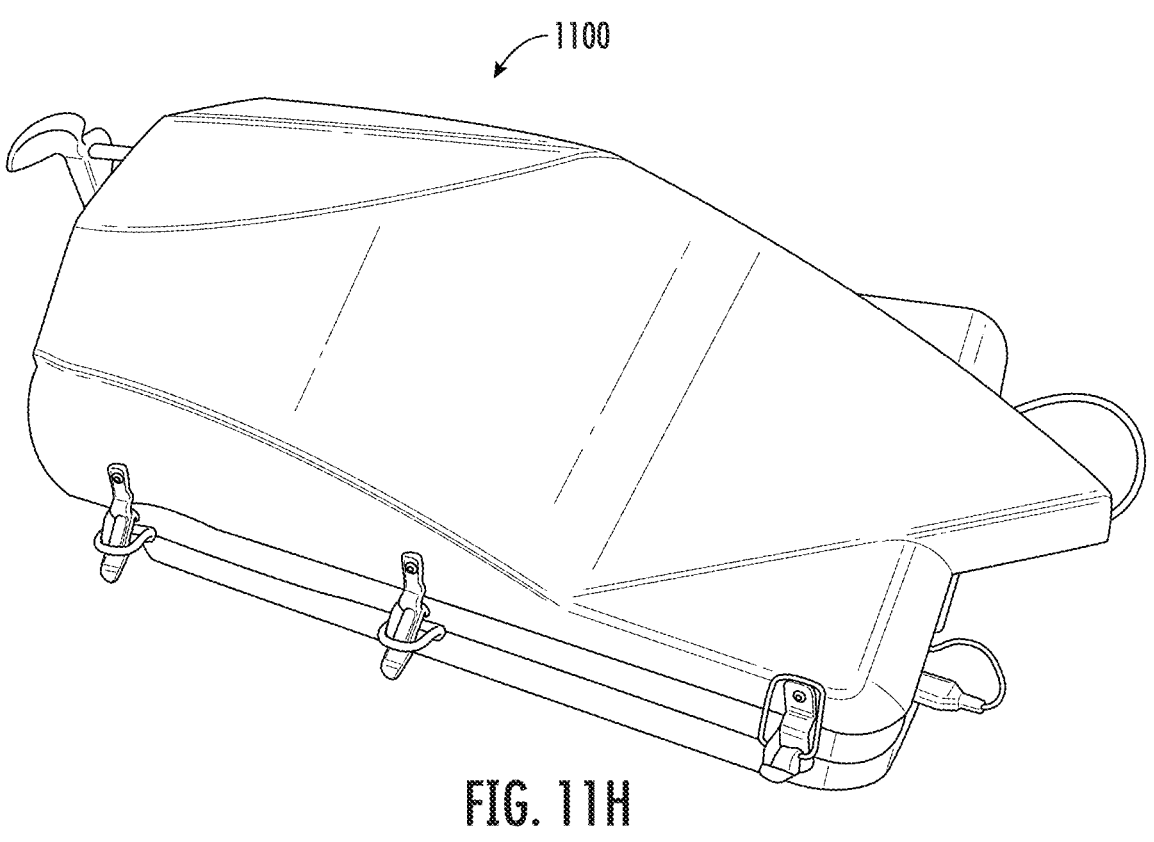
Figure 11I:
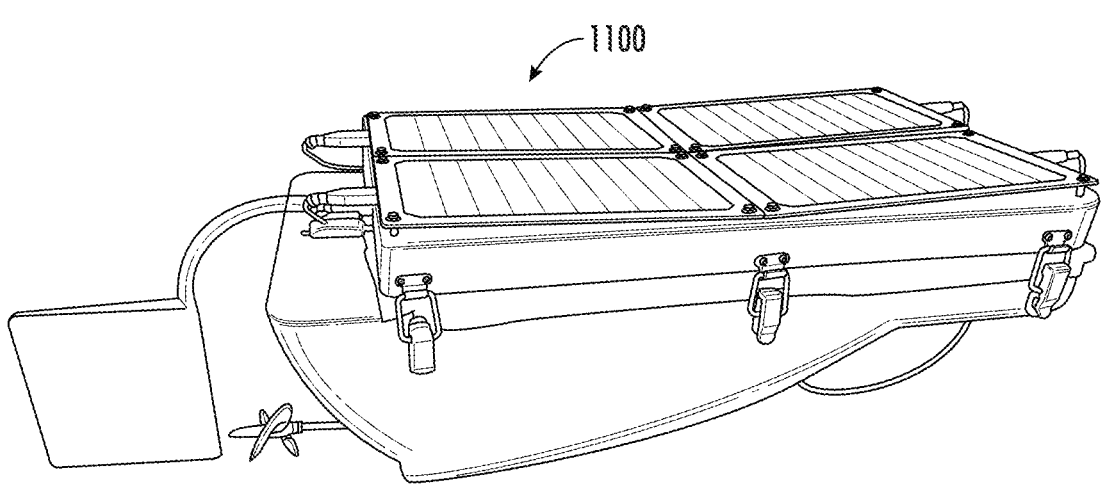

FIG. 11C illustrates a side view of the example implementation 1100 shown in FIGS. 11A and 11B after applying another coat of silver paint to the hull and attaching a lid to the hull with latches. The internal components can be placed inside, and the rudder and propeller are put into place, as shown in FIG. 11D. The solar panel was installed on the top of the hull, as shown in FIG. 11E (perspective view) and FIG. 11F (top view). A perspective view of the bottom of the example implementation 1100 is shown in FIG. 11G, and a view of the bottom of the example implementation from underneath is shown in FIG. 11H. A perspective view of the drone with a rudder attached is shown as FIG. 11I. A test tube carousel 790 was 3D printed for use in the example implementation 1100 illustrated in FIGS. 11A-11I, and the test tube carousel 790 is illustrated and described with respect to FIG. 7F, above.

Example Computing Device

It should be appreciated that the logical operations described herein with respect to the various figures may be implemented (1) as a sequence of computer implemented acts or program modules (i.e., software) running on a computing device (e.g., the computing device described in FIG. 12), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 12, an example computing device 1200 upon which the methods described herein may be implemented is illustrated. It should be understood that the example computing device 1200 is only one example of a suitable computing environment upon which the methods described herein may be implemented. Optionally, the computing device 1200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 1200 typically includes at least one processing unit 1206 and system memory 1204. Depending on the exact configuration and type of computing device, system memory 1204 may be volatile (such as random access memory (RAM)), non-volatile (such as read-only memory (ROM), flash memory, etc.), or some combination of the two. This most basic configuration is illustrated in FIG. 5 by dashed line 1202. The processing unit 1206 may be a standard programmable processor that performs arithmetic and logic operations necessary for operation of the computing device 1200. The computing device 1200 may also include a bus or other communication mechanism for communicating information among various components of the computing device 1200.

Computing device 1200 may have additional features/functionality. For example, computing device 1200 may include additional storage such as removable storage 1208 and non-removable storage 1210 including, but not limited to, magnetic or optical disks or tapes. Computing device 1200 may also contain network connection(s) 1216 that allow the device to communicate with other devices. Computing device 1200 may also have input device(s) 1214 such as a keyboard, mouse, touch screen, etc. Output device(s) 1212 such as a display, speakers, printer, etc. may also be included. The additional devices may be connected to the bus in order to facilitate communication of data among the components of the computing device 1200. All these devices are well known in the art and need not be discussed at length here.

The processing unit 1206 may be configured to execute program code encoded in tangible, computer-readable media. Tangible, computer-readable media refers to any media that is capable of providing data that causes the computing device 1200 (i.e., a machine) to operate in a particular fashion. Various computer-readable media may be utilized to provide instructions to the processing unit 1206 for execution. Example tangible, computer-readable media may include, but is not limited to, volatile media, non-volatile media, removable media and non-removable media implemented in any method or technology for storage of information such as computer readable instructions, data structures, program modules or other data. System memory 1204, removable storage 1208, and non-removable storage 1210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 1206 may execute program code stored in the system memory 1204. For example, the bus may carry data to the system memory 1204, from which the processing unit 1206 receives and executes instructions. The data received by the system memory 1204 may optionally be stored on the removable storage 1208 or the non-removable storage 1210 before or after execution by the processing unit 1206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

REFERENCES

1. Chapra S C, Boehlert B, Fant C, Bierman V J, Henderson J, Mills D, et al. Climate Change Impacts on Harmful Algal Blooms in U.S. Freshwaters: A Screening-Level Assessment. Environ. Sci. Technol. 2017; 51:8933-43.
2. Ng C L, Chen Q Q, Chua J J, Hemond H F. A multi-platform optical sensor for in vivo and invitro algae classification. Sensors (Switzerland). 2017; 17:1-14.
3. Cunha I, Biltes R, Sales M G F, Vasconcelos V. Aptamer-based biosensors to detect aquatic phycotoxins and cya-notoxins. Sensors (Switzerland). 2018; 18:1-34.
4. Wu D, Li R, Zhang F, Liu J. A review on drone-based harmful algae blooms monitoring. Environ. Monit. Assess. 2019; 191.
5. McPartlin D A, Loftus J H, Crawley A S, Silke J, Murphy C S, O'Kennedy R J. Biosensors for the monitoring of harmful algal blooms. Curr. Opin. Biotechnol. [Internet]. Elsevier Ltd; 2017; 45:164-9. Available from: http://dx.doi.org/10.1016/j.copbio.2017.02.018
6. Bickman S R, Campbell K, Elliott C, Murphy C, O'Kennedy R, Papst P, et al. An Innovative Portable Biosensor System for the Rapid Detection of Freshwater Cyanobacterial Algal Bloom Toxins. Environ. Sci. Tech-nol. American Chemical Society; 2018; 52:11691-8.
7. Beckler J S, Arutunian E, Moore T, Currier B, Milbrandt E, Duncan S. Coastal Harmful Algae Bloom Monitoring via a Sustainable, Sail-Powered Mobile Platform. Front. Mar. Sci. 2019; 6:1-14.
8. Shuchman R, Binding C, Leshkevich G, Ortiz J. Remote sensing of harmful algal blooms (HABs) in Lake Erie and other surrounding inland waters: Foreword to special section. J. Great Lakes Res. [Internet]. International Asso-ciation for Great Lakes Research; 2019; 45:403-4. Avail-able from: https://doi.org/10.1016/j.jglr.2019.03.015
9. Seltenrich N. New tools for detecting, monitoring, and preventing harmful Algal Blooms. Environ. Health Per-spect. Public Health Services, US Dept of Health and Human Services; 2014; 122.
10. Birch J. Collecting and processing samples in remote and dangerous places: the Environmental Sample Proces-sor as a case study. PURE Appl. Chem. GENTHINER-STRASSE 13, D-10785 BERLIN, GERMANY:WALTER DE GRUYTER GMBH; 2018; 90:1625-30.
11. Bartram J, Ballance R. Water Quality Monitoring—A Practical Guide to the Design and Implementation of Freshwater Quality Studies and Monitoring Programmes [Internet]. United Nations Environment Programme and the World Health Organization; 1996 [cited 2010 Sep. 20]. Available from: https://archive.epa.gov/water/ar-chive/web/html/vms50.html
12. US Environmental Protection Agency. Sustainability Primer [Internet]. 2015. Available from: https://www.epa.gov/sites/production/files/2015-05/documents/sustainability_primer_v9.pdf
13. US Environmental Protection Agency: Office of Water. A Compilation of Costs Data Associated with the Impacts and Control of Nutrient Pollution [Internet]. 2015. Avail-able from: https://www.epa.gov/sites/production/files/2015-04/documents/nutrient-economics-report-2015.pdf
14. Dodds, W. K., W. W. Bouska, J. L. Eitzmann, T. J. Pilger, K. L. Pitts, A. J. Riley, J. T. Schloesser and DJT. Eutro-phication of U.S. Freshwaters: Analysis of Potential Eco-nomic Damages. Environ. Sci. Technol. Policy Anal. American Chemical Society; 2009. p. 12-9.
15. National Centers for Coastal Ocean Science. NCCOS Joins USGS in Congressional Briefing on Harmful Algal Bloom Threats [Internet]. 2017. Available from: https://coastalscience.noaa.gov/news/nccos-joins-usgscongres-sional-briefing-harmful-algal-bloom-threats/
[1A] "The Jar and Stick Tests," KD HEKS. [Online]. Avail-able: https://www.kdheks.gov/algae-illness/download/Jar_Test.pdf. [Accessed: 3 Mar. 2021].
[2A] D. G. Ullman, The Mechanical Design Process, 6th ed. David Ullman LLC.
[3A] Wang L, Chen W, Xu D, Shim B S, Zhu Y, Sun F, Liu L, Peng C, Jin Z, Xu C, Kotov N A. Simple, rapid, sensitive, and versatile SWNT-paper sensor for environ-mental toxin detection competitive with ELISA. Nano Lett. 2009 December; 9(12):4147-52. doi:10.1021/n1902368r. PMID: 19928776; PMCID: PMC2793542.
[4A] Sarah R. Bickman, Katrina Campbell, Christopher Elliott, Caroline Murphy, Richard O'Kennedy, Philip Papst, and Michael J. Lochhead Environmental Science & Technology 2018 52 (20), 11691-11698 DOI: 10.1021/acs.est.8b02769
[5A] Grattan L M, Holobaugh S, Morris J G Jr. Harmful Algal Blooms and Public Health. Harmful Algae. 2016 July; 57(B):2-8. doi: 10.1016/j.hal.2016.05.003. PMID: 27691671; PMCID: PMC5016795.
[6A] Adriana Zingone, Henrik Oksfeldt Enevoldsen, The diversity of harmful algal blooms: a challenge for science and management, Ocean & Coastal Management, Volume 43, Issues 8-9, 2000, Pages 725-748, ISSN 0964-5691,
[7A] D. M. Anderson, A. D. Cembella, and G. M. Hallegra-eff, "Progress in understanding harmful algal blooms (HABs): Paradigm shifts and new technologies for research, monitoring and management," Annual Review of Marine Science, vol. 4, pp. 143-176, September 2011.

Although the subject matter has been described in lan-guage specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:
1. An automated system for detecting harmful algae blooms, the system comprising:
a plurality of autonomous watercraft; and
a computing device operably connected to the plurality of autonomous watercraft over a network, the computing device comprising a processor and a memory, the memory having computer-executable instructions stored thereon that, when executed by the processor, cause the processor to:
receive remote imaging data of a body of water;
input the remote imaging data to a trained machine learning model configured to generate a geotagged harmful algal bloom (HAB) probability map;
determine a deployment strategy for the plurality of autonomous watercraft based on the geotagged HAB probability map; and
transmit one or more control signals to the plurality of autonomous watercraft based on the deployment strategy, wherein the plurality of autonomous water-craft are configured to collect and analyze a plurality of water samples to obtain a plurality of temporally and spatially resolved water sample measurements; and
output for display a map overlaying the temporally and spatially resolved water sample measurements and the geotagged HAB probability map.

2. The system of claim 1, wherein the one or more control signals are configured to deploy the plurality of autonomous watercraft to a high probability region of the geotagged HAB probability map.

3. The system of claim 1, wherein the memory has further computer-executable instructions stored thereon that, when executed by the processor, cause the processor to receive, from the plurality of autonomous watercraft, temporally- and spatially-resolved water sample data.

4. The system of claim 3, wherein the memory has further computer-executable instructions stored thereon that, when executed by the processor, cause the processor to overlay the temporally- and spatially-resolved water sample data on a map of the body of water.

5. The system of claim 1, wherein one or more of the plurality of autonomous watercraft comprise a sensor configured to detect a harmful algae bloom indicator.

6. The system of claim 5, wherein the sensor comprises one or more of a fluorescence-based sensor, a phosphorus detection sensor, a nitrogen detection sensor, a temperature sensor, a salinity sensor, a pH sensor, a dissolved oxygen sensor, an ultrasound sensor, a light detection and ranging (LIDAR) sensor, an imaging sensor, or a photoelectric sensor.

7. The system of claim 1, wherein one or more of the plurality of autonomous watercraft comprises a sensor system configured to detect a harmful algae bloom indicator.

8. The system of claim 7, wherein the sensor system comprises one or more of a liquid chromatography-mass spectrometry (LC-MS) system or an assay system.

9. The system of claim 1, wherein the remote imaging data comprises imaging data from one or more of a satellite, an aircraft, or a drone.

10. The system of claim 1, wherein the remote imaging data comprises imaging data captured by one or more of a Sea-viewing Wide Field-of-view Sensor (SeaWiFS), a moderate resolution imaging spectroradiometer (MODIS), an advanced very-high-resolution radiometer (AVHRR), or an airborne visible/infrared spectrometer (AVIRIS).

11. The system of claim 1, wherein the step of receive remote imaging data at the body of water comprises receiving weather or water data, the weather or water data comprising one or more of water temperature, water salinity, wind speed and/or direction, or water current speed and/or direction.

12. The system of claim 1, wherein the map overlaying the temporally and spatially resolved water sample measurements comprises an ensemble model.

13. The system of claim 1, wherein the step of determining the deployment strategy for the plurality of autonomous watercraft comprises using a resource mapping model.

14. The system of claim 13, wherein the resource mapping model is a Markov chain model, a Monte Carlo simulation model, a random forest model, a deep learning model, an agent-based model, or an evolutionary model.

15. The system of claim 1, further comprising one or more autonomous aerial vehicles (UAVs) operably coupled to the computing device over the network, wherein the one or more UAVs are configured to collect remote imaging data of algae growth and/or collect and analyze the water samples.

16. A method for detecting harmful algae blooms, the method comprising:

providing a plurality of autonomous watercraft;
    receiving remote imaging data of a body of water;
    inputting the remote imaging data to a trained machine learning model configured to generate a geotagged harmful algal bloom (HAB) probability map;

deploying the plurality of autonomous watercraft based on a deployment strategy, wherein the deployment strategy is based on the HAB probability map;
    collecting, using the plurality of autonomous watercraft, a plurality of water samples to obtain a plurality of temporally and spatially resolved water sample measurements; and
    outputting for display a map overlaying the temporally and spatially resolved water sample measurements and HAB probability map.

17. The method of claim 16, further comprising receiving, from the plurality of autonomous watercraft, temporally- and spatially-resolved water sample data.

18. The method of claim 17, further comprising overlaying the temporally- and spatially-resolved water sample data on a map of the body of water.

19. The method of claim 16, wherein the remote imaging data comprises imaging data from one or more of a satellite, an aircraft, or a drone.

20. The method of claim 16, wherein the remote imaging data comprises imaging data captured by one or more of a Sea-viewing Wide Field-of-view Sensor (SeaWiFS), a moderate resolution imaging spectroradiometer (MODIS), an advanced very-high-resolution radiometer (AVHRR), or an airborne visible/infrared spectrometer (AVIRIS).

21. The method of claim 16, further comprising receiving weather or water data, the weather or water data comprising one or more of water temperature, water salinity, wind speed and/or direction, or water current speed and/or direction and inputting the weather or water data into the trained machine learning model.

22. The method of claim 16, wherein the map overlaying the temporally and spatially resolved water sample measurements comprises an ensemble model.

23. The method of claim 16, wherein the step of determining the deployment strategy for the plurality of autonomous watercraft comprises using a resource mapping model.

24. The method of claim 23, wherein the resource mapping model is a Markov chain model, a Monte Carlo simulation model, a random forest model, a deep learning model, an agent-based model, or an evolutionary model.

25. A computing system for detecting harmful algae blooms, the system comprising:

a processor; and
    a memory operably coupled to the processor, the memory having computer-executable instructions stored thereon that, when executed by the processor, cause the processor to:
        receive remote imaging data of a body of water;
        input the remote imaging data to a trained machine learning model configured to generate a geotagged harmful algal bloom (HAB) probability map;
        determine a deployment strategy for a plurality of autonomous watercraft based on the geotagged harmful algal bloom (HAB) probability map; and
        transmit one or more control signals to the plurality of autonomous watercraft based on the deployment strategy, wherein the plurality of autonomous watercraft are configured to collect and analyze a plurality of water samples to obtain a plurality of temporally and spatially resolved water sample measurements; and
        output for display a map overlaying the temporally and spatially resolved water sample measurements and HAB probability map.

* * * * *